(12) United States Patent
Hwang

(10) Patent No.: US 12,089,817 B2
(45) Date of Patent: Sep. 17, 2024

(54) CONTROLLER FOR SELECTIVELY CONTROLLING MANUAL OR ROBOTIC OPERATION OF ENDOSCOPE PROBE

(71) Applicant: CANON U.S.A., INC., Melville, NY (US)

(72) Inventor: Charles George Hwang, Wellesley, MA (US)

(73) Assignee: Canon U.S.A., Inc., Melville, NY (US)

(*) Notice: Subject to any disclaimer, the term of this patent is extended or adjusted under 35 U.S.C. 154(b) by 713 days.

(21) Appl. No.: 17/165,645

(22) Filed: Feb. 2, 2021

(65) Prior Publication Data
US 2021/0259521 A1    Aug. 26, 2021

Related U.S. Application Data

(60) Provisional application No. 62/979,748, filed on Feb. 21, 2020.

(51) Int. Cl.
*A61B 1/005* (2006.01)
*A61B 34/00* (2016.01)
(Continued)

(52) U.S. Cl.
CPC ............ *A61B 1/0052* (2013.01); *A61B 34/35* (2016.02); *A61B 1/0055* (2013.01); *A61B 1/0057* (2013.01);
(Continued)

(58) Field of Classification Search
CPC ... A61B 1/0052; A61B 1/00105; A61B 34/30; A61B 34/34; A61B 2034/301;
(Continued)

(56) References Cited

U.S. PATENT DOCUMENTS 2,975,785 A    3/1961 Sheldon
3,253,524 A    5/1966 Ashizawa et al.
(Continued)

FOREIGN PATENT DOCUMENTS

JP    H 08-215205 A    8/1996
JP    H 10-262900 A    10/1998
(Continued)

OTHER PUBLICATIONS

Berthet-Rayne, P., et al., "The i2Snake Robotic Platform for Endoscopic Surgery", Ann Biomed Eng., Oct. 2018, pp. 1663-1675, vol. 46, No. 10.
(Continued)

*Primary Examiner* — Anh Tuan T Nguyen
*Assistant Examiner* — Rynae E Boler
(74) *Attorney, Agent, or Firm* — Canon U.S.A., Inc., IP Division

(57) ABSTRACT

A system configured to control an endoscope probe either in manual mode or in robotic mode. The system comprises: a handle at a proximal end of the probe; a handheld controller attachable to the handle; and a robotic controller in communication with the handle and/or the handheld controller. The handheld controller includes separate controls for the manual and robotic modes. In manual mode, the handheld controller combined with the handle and the probe is used to manually control insertion and actuation of the probe into a first location of a lumen. In robotic mode, the handheld controller is removed from the handle, and the robotic controller controls handle to robotically navigate the probe to a second location within the lumen. Attachment and detachment of handheld controller to the handle is such that only certain controls appropriate to a particular portion of a workflow are accessible to the user.

14 Claims, 10 Drawing Sheets

(51) Int. Cl.
  *A61B 34/30* (2016.01)
  *A61B 34/35* (2016.01)
(52) U.S. Cl.
  CPC ... *A61B 2034/301* (2016.02); *A61B 2034/742* (2016.02); *A61B 2034/743* (2016.02)
(58) Field of Classification Search
  CPC ........ A61B 2034/742; A61B 2034/743; A61B 90/50; A61B 34/35
  See application file for complete search history.

(56) References Cited

U.S. PATENT DOCUMENTS

| | | | |
|---|---|---|---|
| 3,610,231 | A | 10/1971 | Takahashi |
| 3,788,303 | A | 1/1974 | Hall |
| 4,207,873 | A | 6/1980 | Kruy |
| 5,355,871 | A | 10/1994 | Hurley et al. |
| 9,737,373 | B2 | 3/2017 | Schuh |
| 9,839,481 | B2 | 12/2017 | Blumenkranz et al. |
| 10,194,906 | B2 | 2/2019 | Auld et al. |
| 10,470,831 | B2 | 6/2019 | Cohen et al. |
| 10,881,280 | B2 | 1/2021 | Baez et al. |
| 2002/0133077 | A1* | 9/2002 | Edwardsen ............ A61B 1/273 600/462 |
| 2007/0135803 | A1 | 6/2007 | Belson |
| 2010/0041949 | A1 | 2/2010 | Tolkowsky |
| 2012/0078053 | A1 | 3/2012 | Phee et al. |
| 2014/0222023 | A1* | 8/2014 | Kim ........................ A61B 34/30 606/130 |
| 2018/0049794 | A1* | 2/2018 | Swayze ................... A61B 34/35 |
| 2018/0049795 | A1* | 2/2018 | Swayze .............. A61B 18/1445 |
| 2019/0261830 | A1 | 8/2019 | Banik et al. |
| 2020/0060516 | A1* | 2/2020 | Baez, Jr. ................. A61B 34/70 |

FOREIGN PATENT DOCUMENTS

| | | |
|---|---|---|
| JP | 2005-237964 A | 9/2005 |
| WO | 2009/069394 A1 | 6/2009 |
| WO | 2012/046605 A1 | 4/2012 |

OTHER PUBLICATIONS

Rozeboom, E.D., "Feasibility of joystick guided colonoscopy", J Robotic Surg., 2015, pp. 173-178, No. 9.

* cited by examiner

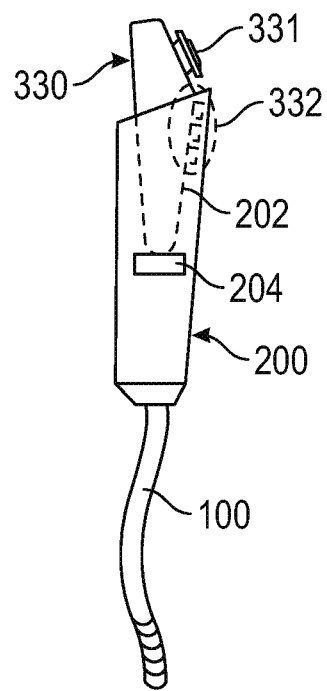
FIG. 3A
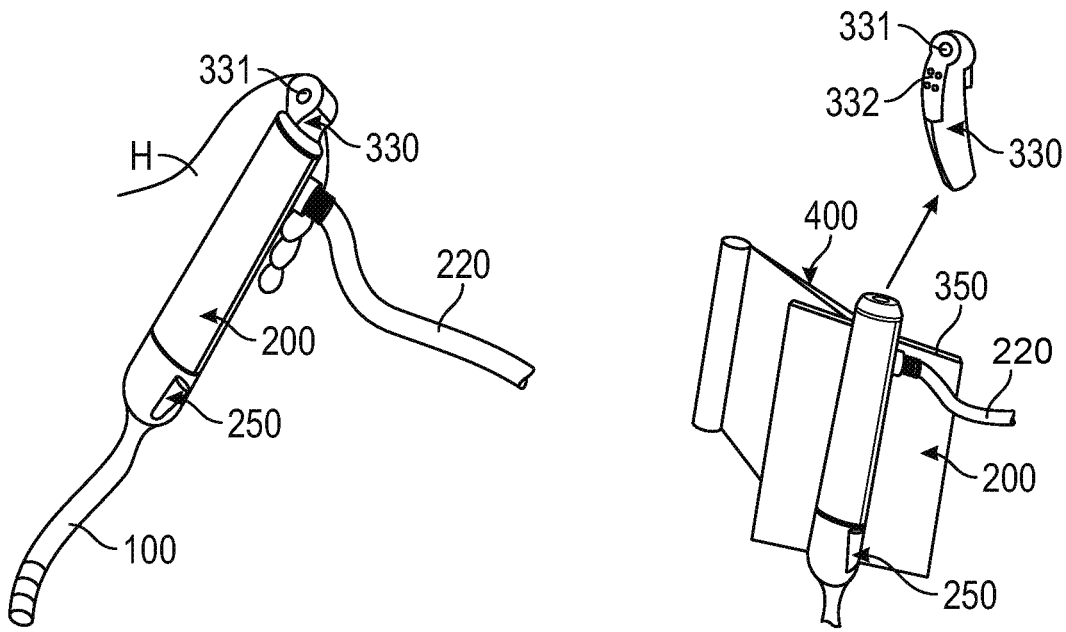
FIG. 3B
FIG. 3C

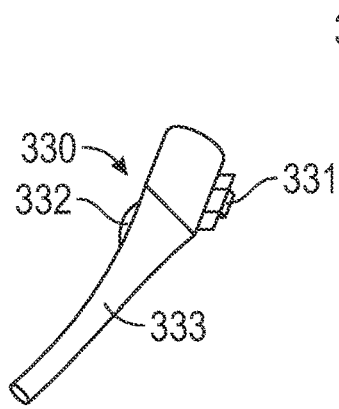
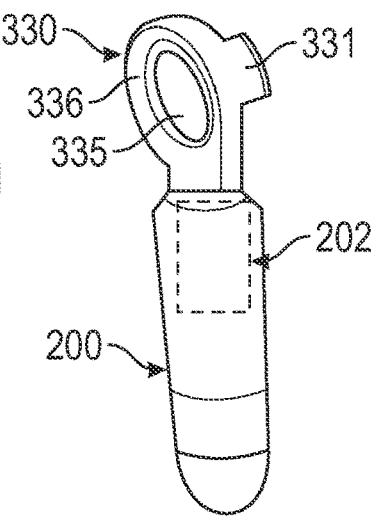
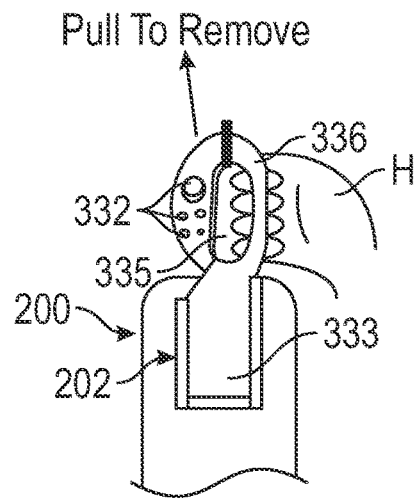
FIG. 4A    FIG. 4B    FIG. 4C
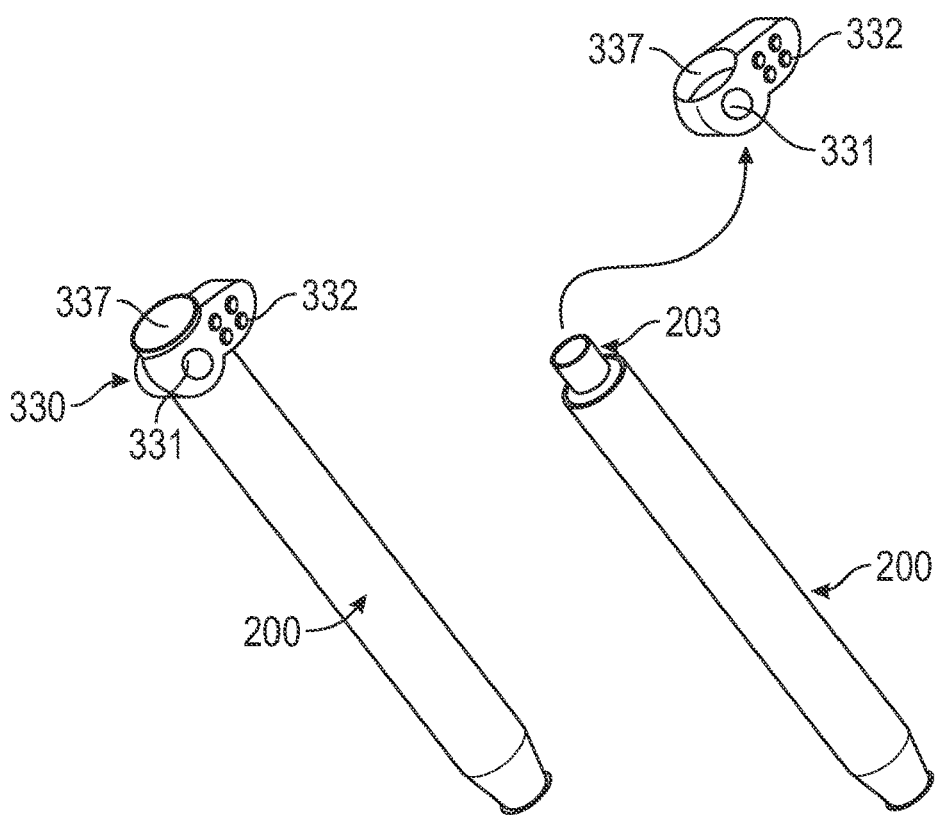
FIG. 5A    FIG. 5B

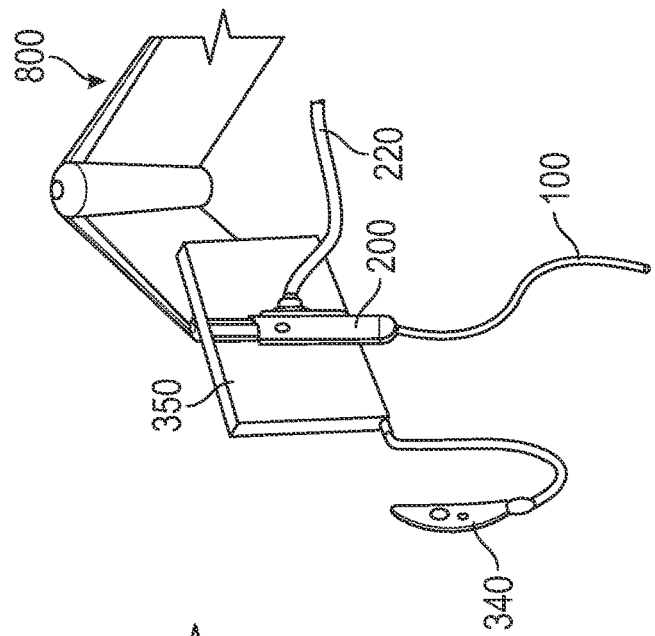
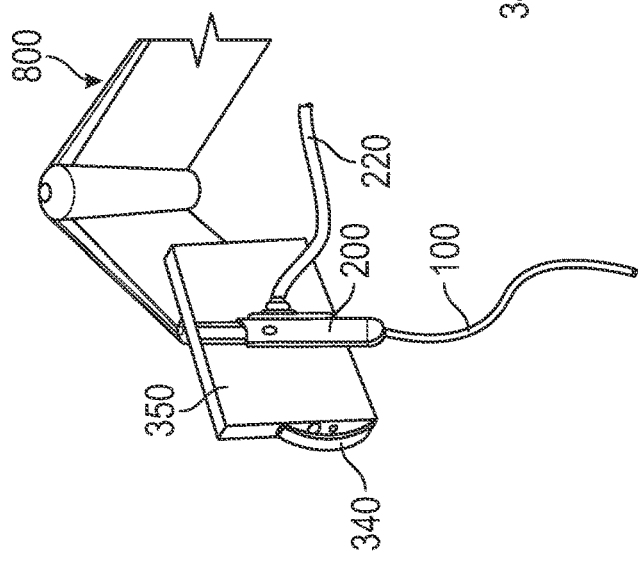
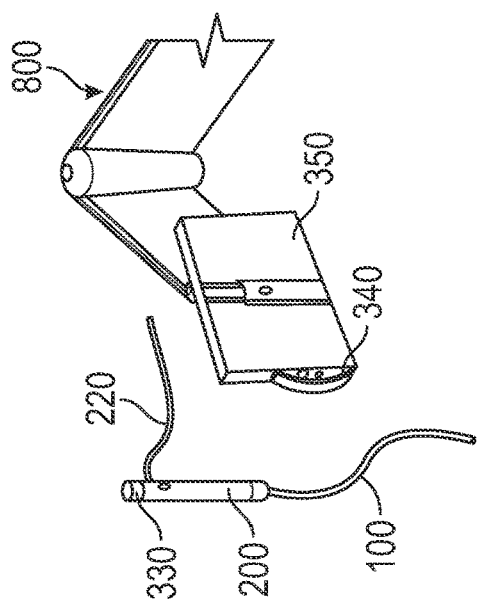

CONTROLLER FOR SELECTIVELY CONTROLLING MANUAL OR ROBOTIC OPERATION OF ENDOSCOPE PROBE

CROSS-REFERENCE TO RELATED APPLICATIONS

The present application claims priority to U.S. provisional applications No. 62/979,748 filed Feb. 21, 2020, the disclosures of which is hereby incorporated by reference in its entirety for all purposes. Priority benefit is claimed under 35 U.S.C. § 119(e).

BACKGROUND INFORMATION

Field of Disclosure

The present disclosure generally relates to medical devices. More particularly, the present disclosure exemplifies various embodiments of a controller interface applicable to interchangeable manual and robotic control for an articulated steerable medical device having a manual insertion mode and a robotically controlled navigation mode to guide interventional tools and instruments, such as endoscopes and catheters, through intraluminal tortuous paths.

Description of Related Art

Endoscopy is a medical procedure allowing remote inspection, manipulation, and/or treatment of internal organs using flexile devices inserted through natural orifices. The complexity of anatomical pathways in a patient, the limited flexibility of existing instruments, and the need to use multiple instruments limit such procedures. Endoscopes are generally composed of a passive proximal section and an active distal section. The proximal passive section can be rigid, semi-rigid, or flexible. The active distal section includes a steerable tip that is remotely actuated by control wires connected to actuation wheels located on the handle of the device. Endoscopes are typically equipped with an imaging device (a camera), a light source, irrigation and/or suction channels, and at least one instrument channel for passing interventional tools. Typical endoscopic instruments have at least 3 degrees of freedom (3DOF) which allow for insertion, rotation and grasping operations. However, confined workspaces and limited visibility of target organs further limit the usability of these systems and require one or more highly skilled endoscopists to perform dexterous tasks. For example, four hands are required to manually control the endoscope and its instruments during a simple procedure. To that end, an endoscopist needs to master a combination of accurate tip angulations, shaft management, and instrument insertion procedures, while communicating with an endoscopist assistant to actuate the instrument and hold the endoscopic shaft in a correct position. To alleviate the complexity of such procedures, several innovative techniques have been proposed. In particular, robotic endoscope systems have been developed.

The following list of patent and non-patent publications provides some examples of manual and robotic endoscope systems. U.S. Pat. Nos. 2,975,785, 3,253,524, 3,610,231, 3,788,303, 4,207,873, 5,355,871, 9,737,373, U.S. Ser. No. 10/470,831, US 20100041949, US 20120078053, US 20190261830, Pierre Berthet-Rayne, et al., "The i2Snake Robotic Platform for Endoscopic Surgery", Ann Biomed Eng. 2018 October;46(10):1663-1675, 2018; and Esther D. Rozeboom, et al., "Feasibility of joystick guided colonoscopy", J Robotic Surg. 9:173-178, 2015. All of the foregoing patent and non-patent publications are incorporated by reference herein in their entirety.

However, even a robotic endoscope system can benefit from a combination of manually controlled insertion and robotically controlled navigation. To achieve this requirement, an endoscopist (a user) must interact with the correct control mechanism at the correct time. In general, a predefined workflow usually defines the correct control to use for manual insertion and for robotically controlled navigation. However, due to recent increased interest in robot-assisted technologies and the need to reduce the instrument's size, it is important to outline the combination of techniques that maximizes technological advancements while minimizing procedural time and optimizing patient safety.

For example, in robot-assisted bronchoscopy, the system requires a manual insertion of the catheter to a predetermined location (the first carina of the patient lungs), and robot-assisted navigation thereafter. While the manual operation is an almost linear insertion, there is still a need to steer the tip of the endoscope during the manual insertion to avoid or at least minimize patient discomfort. Therefore, some control mechanism is necessary even for manual insertion. On the other hand, once the endoscope tip has reached the first carina, the user can release manual control and change to robot-assisted navigation. To that end, it is desirable that the user could perform a handoff procedure in which the insertion of interventional tools, such as endoscopes and catheters, could seamlessly transition between manual insertion and robotic-assisted navigation. However, the known state of the art does not satisfy these needs.

One challenge in achieving a seamless transition from manual to robotic control is that if the user operates the same controller interface for manual insertion and for robotic operation mode, the access to functionality must be appropriate for each mode. More specifically, in order to avoid accidents and increase patient safety, there is a need for robotic controls that should not be accessible to the user during manual insertion and manual controls that should not be accessible during robotic-assisted mode.

SUMMARY OF EXEMPLARY EMBODIMENTS

According to at least one embodiment of the present disclosure, an endoscope system comprises features for manual controlled endoscope and for robotic controlled endoscopic instruments, and a control device which selectively controls the two functionalities. In one embodiment, there is provided an endoscope control system comprising: an endoscope probe having a handle and tubular shaft extending from the handle to a distal end thereof; a handheld controller attachable to and detachable from the handle, and a robotic controller in communication with the handheld controller and/or with the handle. The endoscope control system is configured to operate in a manual mode and in a robotic mode. In the manual mode, the handheld controller is attached to the handle of the endoscope and is used to manually control the movement of a distal portion of the tubular shaft; and, in the robotic mode, the robotic controller controls the movement of the entire endoscope. The endoscope system is applicable to interchangeable manual and robotic control for an articulated steerable medical device having manual insertion mode and robotically controlled navigation mode to guide interventional tools and instruments, such as endoscopes and catheters, through intraluminal tortuous paths.

Advantageously, according to the various embodiments of the present disclosure, when the handheld controller is attached to the handle of the endoscope, minimal controls are accessible to the user. One purpose of this configuration is for manual insertion of the endoscope into a luminal cavity. To that end, a simple joystick or directional keypad provides the functionality available to control movement (mainly directionality) of the tip of the endoscope. Other controls, such as buttons for irrigation or suction, are deactivated or hidden within the handle of the endoscope, thereby eliminating the possibility of inadvertent activation and/or confusion by the user. After manual positioning of the endoscope tip to a predetermined position in an intraluminal cavity, the handle of the endoscope is docked on a support platform or arm of the robotic system. Once the handle is docked to the support platform or arm, the system automatically enters a robotic mode for guiding the endoscope to the desired region of interest.

According to one embodiment, the handheld controller is removable from the handle. To facilitate removing the handheld controller from the handle, the handheld controller is configured to pop up slightly from the handle when available for removal. Once the handheld controller is removed from the handle, the user has access to the complete suite of functions (buttons) provided in the handheld controller. Once a procedure is complete, the handheld controller can be reinserted into the handle for storage and/or for battery recharging.

According to another embodiment, the handheld controller consists of a knob attached on the proximal end (top) of the handle. The knob is configured to turn both clockwise and counter-clockwise by rotating (twisting) the knob with a thumb or two-finger action of a user. This twisting of the knob corresponds to the movement of the catheter or endoscope tip; i.e., twist the knob left causes the tip of the endoscope to turn left; twist the knob right causes the tip to turn right. The knob may have knurls, a gripping texture, or other features to provide an easy grip for accurate control. According to one embodiment, the knob is preferably cylindrical in shape and symmetrical about the length axis of the endoscope handle, and the diameter of the knob is equal to (or smaller than) the diameter of the handle.

According to another embodiment, the handheld controller is configured with an opening for allowing a user's hand to grasp the handheld controller with increased grip ability and improved comfort. According to a further embodiment, the handheld controller includes a hollow connecting part configured to fit on the outer circumference of the handle of the endoscope. In this case, when the handheld controller is removed from the handle, the handheld controller can be used as a finger-held mini-joystick for robot control mode.

According to another embodiment, a controller system (300) is configured to control an endoscope probe (100) to selectively operate in manual mode and/or in robotic mode. The controller system comprises: a handle (200) at a proximal end of the probe; a handheld controller (330) attachable to the handle (200); and a robotic controller (302) in communication with the handle and/or with the handheld controller. The handheld controller has a first control section to be operated under the manual mode and a second control section to be operated under the robotic mode. In the manual mode, the handheld controller is combined with the handle, and the combined handheld controller and handle allow a user to operate the first control section to manually control insertion and movement of a distal portion of the probe. In the robotic mode, the robotic controller cooperates with the handheld controller to prevent user access to the first control section, and allows the user to operate the second control section to robotically control navigation and movement the entire probe.

These and other objectives, features, and advantages of the present disclosure will become apparent upon reading the following detailed description of exemplary embodiments of the present disclosure, when taken in conjunction with the appended drawings, and provided claims.

BRIEF DESCRIPTION OF DRAWINGS

Further aspects will hereinafter be described in conjunction with the appended drawings, provided to illustrate and not to limit the disclosed aspects, wherein like designations denote like elements of the present disclosure.

FIG. 3A shows an embodiment of a handheld controller 330 combined with an endoscope handle 200 configured to generate control signals for an endoscopic probe 100, according to the present disclosure. FIG. 3B shows a perspective view of the handheld controller 330 attached to (inserted into) the handle 200 of the probe 100. FIG. 3C illustrates a configuration where the handle 200 is attached to a support platform 350, and the handheld controller 330 is detached from the handle 200.

FIG. 4A, FIG. 4B, and FIG. 4C show another embodiment of the handheld controller 330, and the manner in which the handheld controller 330 interacts with the endoscope handle 200.

FIG. 5A and FIG. 5B show another embedment of a handheld controller interface 330 which is removably attachable to the endoscope handle 200.

FIG. 8A, FIG. 8B, and FIG. 8C show a method of using the handheld controller 330 in manual mode and robotic mode with a handoff transition between the two modes.

DETAILED DESCRIPTION OF EXEMPLARY EMBODIMENTS

Figure 1A:
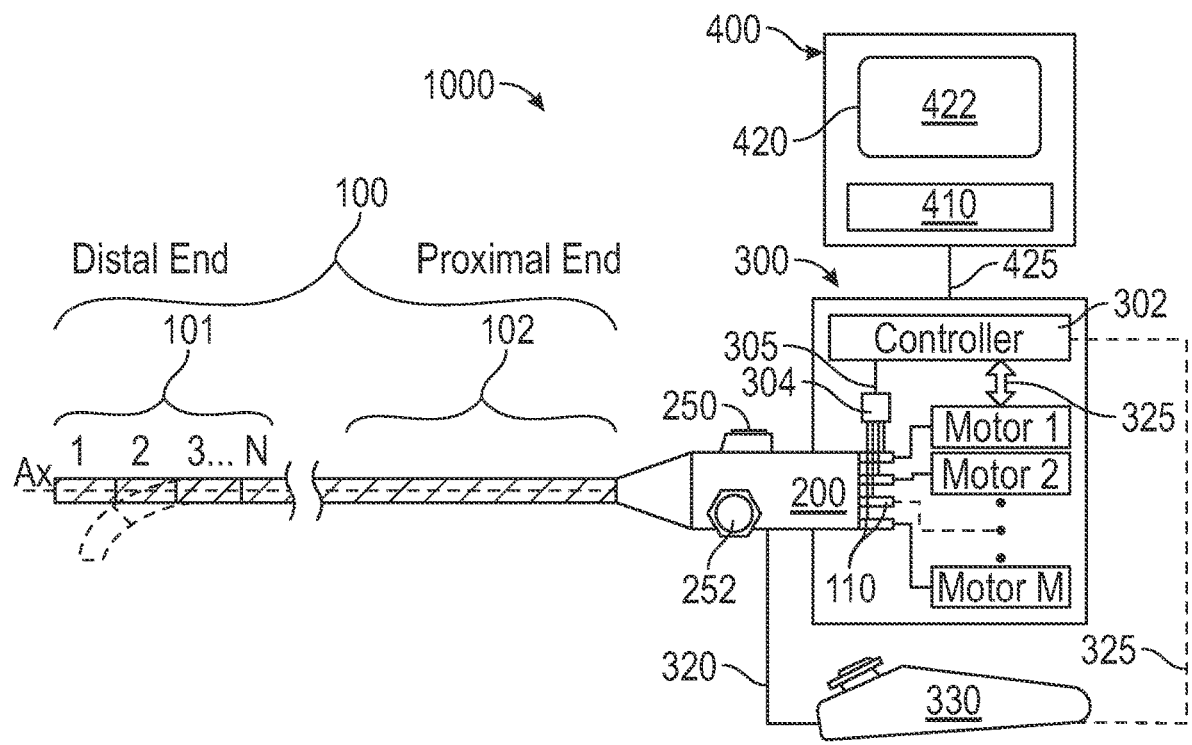
FIG. 1A illustrates an exemplary embodiment of a robotically controlled endoscopic probe 100 having multiple bending sections at the distal end of the probe.

The exemplary embodiments disclosed herein are based on an objective of providing a controller interface applicable to interchangeable manual and robotic control for an articulated steerable medical device having manual insertion mode and robotically controlled navigation mode to guide interventional tools and instruments, such as endoscopes and catheters, through intraluminal tortuous paths.

Throughout the figures, the same reference numerals and characters, unless otherwise stated, are used to denote like features, elements, components or portions of the illustrated embodiments. In addition, while the subject disclosure is described in detail with reference to the enclosed figures, it is done so in connection with illustrative exemplary embodiments. It is intended that changes and modifications can be made to the described exemplary embodiments without departing from the true scope and spirit of the subject disclosure as defined by the appended claims. Although the drawings represent some possible configurations and approaches, the drawings are not necessarily to scale and certain features may be exaggerated, removed, or partially sectioned to better illustrate and explain certain aspects of the present disclosure. The descriptions set forth herein are not intended to be exhaustive or otherwise limit or restrict the claims to the precise forms and configurations shown in the drawings and disclosed in the following detailed description.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached", "coupled" or the like to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown in one embodiment can apply to other embodiments. It will also be appreciated by those of skill in the art that references to a structure or feature that is disposed "adjacent" to another feature may have portions that overlap or underlie the adjacent feature.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without limitation and without departing from structural or functional meaning.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated. Further, in the present disclosure, the transitional phrase "consisting of" excludes any element, step, or component not specified in the claim. It is further noted that some claims or some features of a claim may be drafted to exclude any optional element; such claims may use exclusive terminology as "solely," "only" and the like in connection with the recitation of claim elements, or it may use of a "negative" limitation.

The term "about" or "approximately" as used herein means, for example, within 10%, within 5%, or less. In some embodiments, the term "about" may mean within measurement error. In this regard, where described or claimed, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to include all sub-ranges subsumed therein. As used herein, the term "substantially" is meant to allow for deviations from the descriptor that do not negatively affect the intended purpose. For example, deviations that are from limitations in measurements, differences within manufacture tolerance, or variations of less than 5% can be considered within the scope of substantially the same. The specified descriptor can be an absolute value (e.g. substantially spherical, substantially perpendicular, substantially concentric, etc.) or a relative term (e.g. substantially similar, substantially the same, etc.).

The present disclosure generally relates to medical devices, and it exemplifies embodiments of an optical probe which may be applicable to a spectroscopic apparatus (e.g., an endoscope), an optical coherence tomographic (OCT) apparatus, or a combination of such apparatuses (e.g., a multi-modality optical probe). The embodiments of the optical probe and portions thereof are described in terms of their positon/orientation in a three-dimensional space. As used herein, the term "position" refers to the location of an object or a portion of an object in the three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" refers to the position of an object or a portion of an object in at least one degree of translational freedom and to the orientation of that object or portion of object in at least one degree of rotational freedom (up to a total six degrees of freedom); the term "shape" refers to a set of posture, positions, and/or orientations measured along the elongated body of the object. As it is known in the field of medical devices, the terms "proximal" and "distal" are used with reference to the manipulation of an end of an instrument extending from the user to a surgical or diagnostic site. In this regard, the term "proximal" refers to the portion of the instrument closer to the user, and the term "distal" refers to the portion of the instrument further away from the user and closer to a surgical or diagnostic site.

As used herein the term "catheter" generally refers to a flexible and thin tubular instrument made of medical grade material designed to be inserted through a narrow opening into a bodily lumen (e.g., a vessel) to perform a broad range of medical functions. The more specific term "optical catheter" refers to a medical instrument comprising an elongated bundle of one or more flexible light conducting fibers disposed inside a protective sheath made of medical grade material and having an optical imaging function. A particular example of an optical catheter is fiber optic catheter which comprises a sheath, a coil, a protector and an optical probe. In some applications a catheter may include a "guide catheter" which functions similarly to a sheath.

As used herein the term "endoscope" refers to a rigid or flexible medical instrument which uses light guided by an optical probe to look inside a body cavity or organ. A medical procedure, in which an endoscope is inserted through a natural opening, is called an endoscopy. Specialized endoscopes are generally named for how or where the endoscope is intended to be used, such as the bronchoscope (mouth), sigmoidoscope (rectum), cystoscope (bladder), nephroscope (kidney), bronchoscope (bronchi), laryngoscope (larynx), otoscope (ear), arthroscope (joint), laparoscope (abdomen), and gastrointestinal endoscopes.

In the present disclosure, the terms "optical fiber", "fiber optic", or simply "fiber" refers to an elongated, flexible, light conducting conduit capable of conducting light from one end to another end due to the effect known as total internal reflection. The terms "light guiding component" or "waveguide" may also refer to, or may have the functionality of, an optical fiber. The term "fiber" may refer to one or more light conducting fibers. An optical fiber has a generally transparent, homogenous core, through which the light is guided, and the core is surrounded by a homogenous cladding. The refraction index of the core is larger than the refraction index of the cladding. Depending on design choice some fibers can have multiple claddings surrounding the core.

Specific embodiments of the present disclosure are directed to improving robotically controllable endoscopes or catheters applicable to minimally invasive surgical (MIS) procedures. MIS procedures involve the use of long rigid or flexible surgical instruments that are inserted into the body of a patient through small incisions or natural orifices. There is wide range of well known endoscopic procedures. An important aspect of MIS endoscopy is the ability to "see" inside the body of the patient by directly inserting an imaging device into the area of interest. As the imaging device, most endoscopes use a high-resolution camera and a light source at the endoscope tip. The endoscope tip can be actively steered either manually by two thumb-controlled dials, or by a robotic actuator at the proximal end. Insertion and retraction of the endoscope into the patient body can also be performed either manually or robotically. Throughout this disclosure, working principles and novel improvements for robotic controlled endoscopic devices are described in detail. The application of such endoscopic devices includes procedures for both diagnostic and therapeutic purposes.

<FIG. 1>

Figure 1B:
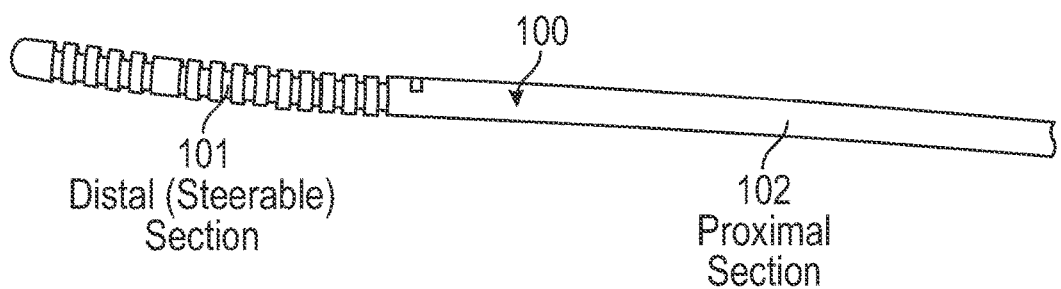
FIG. 1B shows a photograph of an exemplary implementation of the endoscopic probe 100.

A system 1000 configured to control a robotic steerable endoscopic probe 100 either in manual mode or robotic mode is described referring to FIG. 1A and FIG. 1B. FIG. 1A illustrates a general structure of a steerable endoscope probe 100 controlled by a continuum robot system 300 and/or a handheld controller 330, according to one embodiment of the present disclosure. The probe 100 has one or more bendable or steerable sections applicable to catheter- or endoscope-assisted minimally-invasive medical procedures. Specifically, FIG. 1A shows a robotically controlled medical probe 100 having a steerable distal section 101 and a non-steerable proximal section 102 which are arranged along a longitudinal axis (Ax). The non-steerable proximal section 102 is a tubular body (extrusion body) made of extruded or 3D printed polymer material. The steerable distal section 101 is made of a plurality of actuatable segments or disks. The probe 100 is controlled by a robotic control system 300 which is connected to the probe 100 via a handle 200. The control system 300 generally includes a controller 302, e.g., a proportional-integral-derivative (PID) controller or other digital signal processor (DSP) along with suitable software, firmware and peripheral hardware, which are known to persons having ordinary skill in the art. DSPs are generally dedicated integrated circuits; however DSP functionality can also be produced by using field-programmable gate array chips (FPGAs). The control system 300 can be part of, or is connected to, a computer system 400 (e.g., a system console) operated by a processor or central processing unit (CPU) 410. The computer system 400, the robotic control system 300, the handheld controller 330, and the handle 200 are operably connected to each other by a network and/or a cable bundle 425. Among other functions, the computer system 400 can provide a surgeon or other user with an image display device 420 and a graphical user interface (GUI) 422 to interact and remotely operate the probe 100. In the various embodiments disclosed herein, the handheld controller 330 is configured to be connected to the handle 200 via a physical connection such as a wired connection 320 and/or via a wireless connection 325 via the robotic control system 300.

The robotic control system 300 may include a plurality of actuating motors (or actuators) Motor 1 through M, where M is an integer greater than zero and equal to a number of control wires 110 necessary for steering the probe 100. The robotic control system 300 also includes one or more sensors 304. Sensors 304 can include a strain sensor and/or a position sensor. A strain sensor can be implemented by, for example, a strain gauge or a piezo resistor. A strain sensor serves to detect and/or measure compressive or tensile forces (F) exerted on the driven control wire 110. In this case, the strain sensor outputs a signal 305 corresponding to the amount of compressive or tensile force (an amount of strain) being applied to each control wire 110 during actuation of the steerable probe 100. The sensors 304 could also output a signal 305 corresponding to an amount of movement (a distance) of displacement for each actuated control wire 110, during a procedure. A sensor that measures the amount of displacement of the control wire can be implemented by a Hall-effect sensor. The sensor 304 can also be implemented by an electromagnetic (EM) sensor configured to measure and/or detected the position and orientation of the steerable probe 100. The signals 305 from the sensors 304 (strain sensor, displacement sensor, and/or position sensor) for each control wire 110 are fed into the controller 302 to control each motor or actuator individually. In this manner, each control wire 110 can be actively controlled to implement appropriate shaft guidance for navigating the probe 100 through intraluminal cavities of a patient's anatomy. Each electromechanical connection of a control wire 110 with a corresponding motor or actuator is in operative connection with the one or more sensors 304 to create a feedback loop 325 (based on the signal 305) for the controller 302. The controller 302 is used to electronically control the operation (movement) of each control wire 110 based on one or more of tensional, compressive, and/or torsional forces applied to each control wire 110.

The handle 200 provides an electromechanical interface between the probe 100 and the control system 300. For example the handle 200 may provide mechanical, electrical, magnetic, and/or optical connections, and other data/digital connections for interfacing the probe 100 with the control system 300. The handle 200 may also provide an input port 250 that a surgeon or operator could use to insert an instrument or an end effector. For example, the input port 250 can be used to insert small instruments, such as small forceps, needles, or electrocautery instruments and the like. In addition, the handle 200 may include one or more dials or control wheels 252 for controlling the bending (steering) of the distal section 101 of probe 100.

FIG. 1B shows in more detail a photograph of an exemplary probe 100. According to one embodiment, the probe 100 may have an outer diameter of about 0.14 inches, with a distal section 101 being around 2.0 inches in length, and the total length of the probe 100 being about 24 inches. The anchor members are typically constructed from Polyether Block Amide (e.g., Pebax® from Arkema Inc.). The outer sheath which covers much of the probe 100 can also be made from Pebax. However, other plastics are also viable, e.g. polyurethane.

The probe 100 includes a cylindrical tubular shaft which has one or more tool channels and a plurality wire conduits extending from the proximal end to the distal end of the probe. Among the tool channels, the probe 100 may include at least one (some embodiments may have more than one) tool channel extending along (typically inside) the tubular shaft. Among the wire conduits, the probe may include a plurality of wire conduits extending along (typically within) the wall of the tubular shaft (sheath). The one or more tool channels allow access to end effectors located at the distal end of the probe 100. The one or more tool channels may also be used for sending or retrieving liquid or gaseous substances (e.g., air, water) to a target area. The tool channels may also be used for passing imaging components such as optical fibers, miniature cameras, and/or sensors powered by electrical wires. The wire conduits formed within the wall of the sheath allow anchorage and/or passage of control wires and/or support wires used for steering (or bending) the distal section 101 of the sheath. At the proximal end of the probe 100, the handle 200 with the access port 250 and one or more control wheels 252 is used to manually bend the distal (steerable) section 101 in one or more directions.

The probe 100 is configured to provide flexible access to intraluminal target areas with one or more than one bending curves to reach the intended target area near the distal end of the probe, while retaining torsional and longitudinal rigidity so that physicians can control the end effectors located at the distal end of the sheath by maneuvering the handle 200, or by kinematic operation of control system 300. In order to provide such steerable functionality, the probe 100 is equipped with one or more than one support wires (a backbone or tendon), and a plurality of control wires 110 which are arranged inside the wire conduits along (typically inside) the wall of the sheath along the length of the probe 100.

<FIG. 2>

Figure 2A:
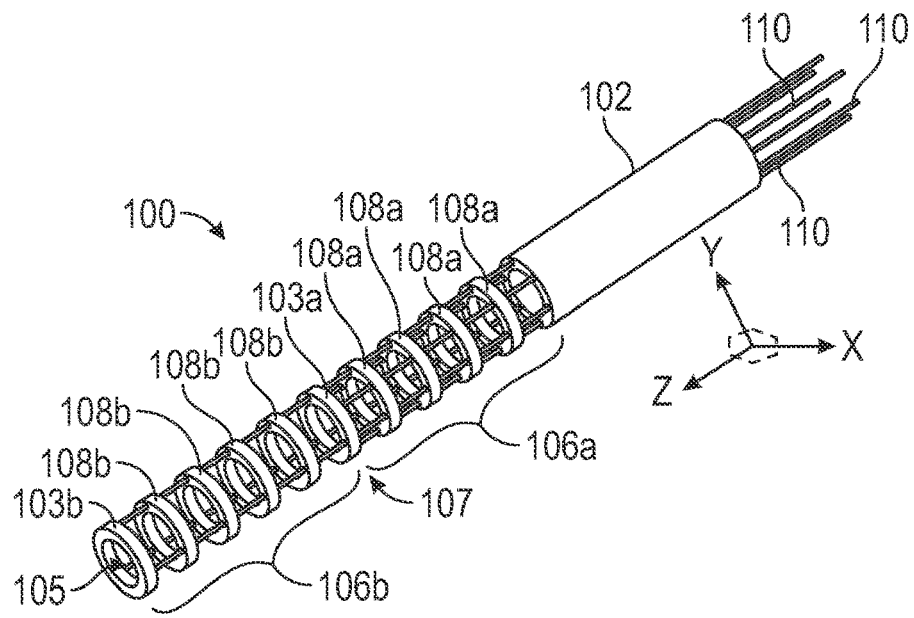
FIG. 2A is a perspective view of an exemplary probe 100 having two bending sections.

The structure and principles of actuation for an example steerable endoscope probe 100 is described with reference to FIG. 2A-FIG. 2C. FIG. 2A is a perspective view of an exemplary probe 100. According to one embodiment, the probe 100 can be a wire-driven continuum robot, which includes a proximal section 102 which is made of a solid sheath, and a distal section 101 with is made of a plurality of disks or guide members grouped into bending sections 106a and 106b with at least one inflection point 107. In the probe 100, shown in FIG. 2A, a plurality of control wires 110 extend from the proximal end to the distal end thereof, passing through conduits 104 along the wall of the sheath, and through a plurality of guide members 108a, 108b, and anchor members 103a, 103b. The sheath of the proximal section 102 and wire-guiding disks of the distal section 101 are arranged along the probe axis Ax to form at least one tool channel 105.

The control wires 110 are arranged in a lengthwise direction parallel to the Z-axis; some control wires 110 are coupled at the inflection point 107 to a first anchor member 103a, and some of the control wires 110 are coupled at the distal end to a second anchor member 103b. All of the control wires 110 are coupled, at the proximal end of the probe 100, to individual motors or actuators (in the control system 300 shown in FIG. 1A) via the handle 200. The control wires 110 can be metal wires, for example, planotype wires, stainless-steel wires, or nickel-titanium-alloy wires. The anchor members 103a and 103b have an annular shape with the center axis thereof extending along the Z-axis direction. The plurality of control wires 110 are fixedly coupled to the anchor members 103a, 103b, for example, by bonding, pinning, welding, pressure fitting, or screw sets.

The proximal section 102 of the probe 100 has a tubular shape with the center axis thereof extending along the Z-axis direction and a plurality of conduits 104 (through holes) extending within the wall of the sheath. The proximal section 102 functions as a support section, which can be flexile (but non-bendable), and thus it has a function of transmitting a force from the actuators or motors to the one or more bending sections, when the control wires passing along the through holes of the sheath are driven in the Z-axis direction, without any buckling or slack of the control wires.

Figure 2B:
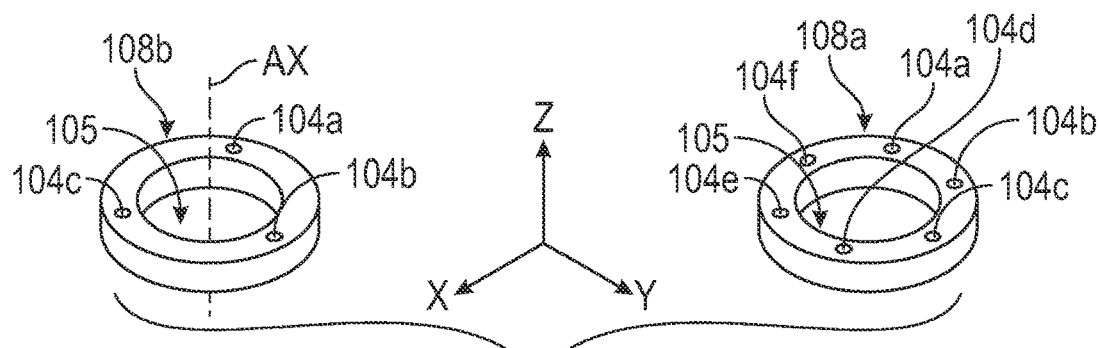
FIG. 2B shows perspective views of representative guide members of a bending section with through holes (guide holes) for guiding control wires.
Figure 2C:
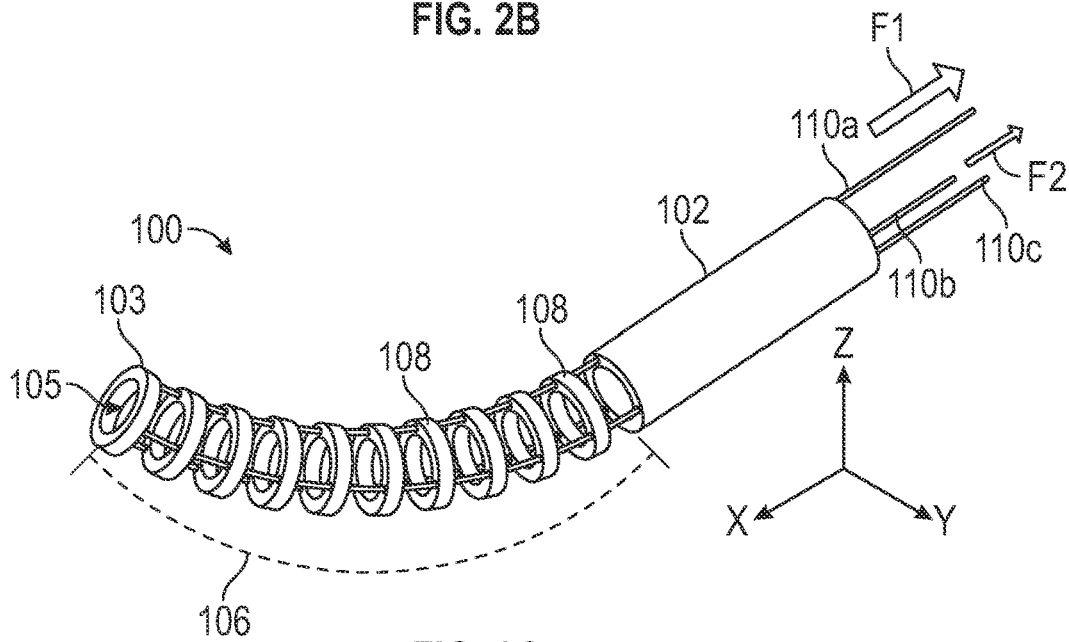
FIG. 2C shows an example of bending or steering a bending section of the probe 100.

FIG. 2B shows a perspective view of a representative guide member 108b and a representative guide member 108a. Each guide member has an annular shape with an opening concentric with the probe axis Ax extending along the Z-axis direction. When these guide members are combined in a lengthwise direction as shown in FIG. 1A, the central opening in the guide members forms the tool channel 105. The guide member 108b has conduits or guide holes 104a, 104b, and 104c extending along the wall of the annular shape of the guide member. The guide holes 104a, 104b, and 104c are configured to allow respective control wires 110 to pass and slide therethrough during navigation (steering) operation of the probe 100. Among the control wires 110, one wire can be fixed to the guide member at the guide hole by, for example, bonding, and the other two control wires are slideable with respect to the guide holes. Since each guide member 108b contacts the control wires 110 through the guide holes, the guide members can include a material such as resin with a low coefficient of friction. The guide member 108a has guide holes 104a, 104b, 104c, 104d, 104e, and 104f to allow passage for control wires 110 of the bending section 106a and bending section 106b. Similar in design to the bending section 106b, the bending section 106a has a plurality of guide members 108a and each guide member has guide holes 104a-104f. The guide holes are arranged to allow the control wires 110 coupled to the anchor member 103b and control wires coupled to the anchor member 103a to pass through the guide holes. One of the three control wires coupled to the anchor member 103a is fixed to a guide hole in each guide member, and the remaining two control wires are slideable with respect to the guide holes.

The bending motion (steering) of the probe 100 when the control wires 110 are actively driven is described next. For simplicity, the bending of a single bending section is explained. As shown in FIG. 2C, a single bending section 106 of a probe 100 includes, from the distal end thereof, an anchor member 103, a plurality of guide members 108, and a support section 102 (sheath) with a plurality of guide holes 104a, 104b, and 104c (as shown in FIG. 2B). Control wires 110a, 110b, and 110c extend from the proximal end to the distal end along the guide holes 104a, 104b, and 104c, respectively. The control wires 110 are fixedly coupled at the distal end thereof to the anchor member 103. The control wires 110 coupled at the distal thereof to anchor member 103 are slideable with respect to the guide members 108 by the action of an actuator or motor connected at the proximal end of each control wire (refer to FIG. 1A). One of the three control wires 110 (e.g., control wire 110b in FIG. 2C) is fixed (or mechanically grounded) with respect to guide members 108, and the remaining two control wires 110 (e.g., control wires 110a and 110c in FIG. 2C) are slideable with respect to the guide holes of the guide member 108.

In bending the distal section of probe 100, each control wire 110 is individually controlled by a respective actuator or motor. For example, in FIG. 2C, while control wire 110b may be fixed or anchored to anchor member 103, a control wire 110a is pulled with a control force F1, and a control wire 110c is pulled with a control force F2 (control force F2 is lower than control force F1, in this example). In this manner, the bending section 106 can be bent in a desirable direction, in accordance with a combination of the driving amounts of linear displacement of control wires 110a and 110c. To control the posture of the distal end of the probe 100, driving two of the three control wires is sufficient. However, to bend more than one section of the probe 100, each bendable section needs to be controlled by actuating one or more control wires 110.

While the case of driving the control wires anchored at the distal end of a single bending section has been described above with respect to FIG. 2C, if control wires of all bending sections of FIG. 2A are driven, the postures of each bending section may be independently controlled in accordance with the driving amounts of the individual control wires. Further, a mechanism that rotates the wire-driven probe 100 around the Z-axis may be additionally provided. In the case of providing rotation to the probe, a bending section may be bent in a desirable direction by driving only one control wire and rotating the entire sheath and control wires included therein.

In general, either during insertion or retraction of the probe 100, the center line of the lumen is the desired trajectory to be followed during active control of the bending sections. To that end, recently proposed steerable instruments, such as guided catheters or endoscopes, have attempted to implement various concepts of shaft guidance systems with the goal of forcing the flexible shaft to keep to the desired trajectory. In one example (see, e.g., US 2007/0135803), when using a shaft guidance system, the steerable instrument is advanced through a lumen while sensors 304 measure the insertion depth of the shaft-guide and the angulations of user-controlled steerable tip segments to obtain trajectory information. The trajectory information is stored in a memory of the system. After a short advance in insertion depth, the shape of the steerable shaft-guide is corrected by adjusting (rotating or bending) segments of the instrument in such a way that the new shape closely matches the desired trajectory. This process is repeated until a target area is reached. Accordingly, a procedure can take a long time, which is not convenient or comfortable for the patient.

Therefore, before performing robotic controlled navigation, it is desirable to manually insert the probe 100 to a predetermined location. For example, in robot-assisted bronchoscopy, the system requires a manual insertion of the catheter to the first carina of the patient lungs, and robot-assisted navigation thereafter. However, the probe can contact the patient's anatomy and this can cause discomfort and/or pain to the patient. Therefore, some control mechanism is necessary even for manual insertion.

<FIG. 3>

A first embodiment of a handheld controller 330 configured to be removably attached to an endoscope handle 200 is described with reference to FIG. 3A-FIG. 3C. FIG. 3A shows an embodiment of a controller interface for manual operation, according to the present disclosure. The controller interface includes a handheld controller 330 which includes a first control section 331 (a first control interface) and a second control section 332 (a second control interface). The first control section 331 includes, for example, a joystick or directional keypad interface, and the second control section 332 includes a plurality of control buttons or switches. An example of a joystick is a multi-axis (e.g., six axis) joystick used in gamepad controllers such as the NintendoSwitch® handheld controller. An example of a directional keypad includes a cross-shaped directional keypad such as a console D-pad as used in gaming consoles like PlayStation® or Xbox®. The first control section 331 is configured to mainly control actuation of directionality (angular movement) of the steerable portion of the probe 100. On the other hand, the second control section 332 is configured to mainly control operations concerning an interventional procedure such as activating irrigation or suction, operating end effectors (tools inserted through the probe) to perform an interventional procedure (e.g., actuating biopsy or ablation tools). Naturally, the functions of the first control section 331 and second control section 332 can be interchangeable and/or combined with each other. However, for purposes of this disclosure, it is advantageous to limit the functionality of each control section of the handheld controller according to the operation mode (either manual mode or robotic mode) of the endoscope system. Moreover, in a case where the manual operation of any function of the handheld controller can pose a hazard, a transition mode is provided where all functions of the controller can be momentarily disabled or suppressed.

As shown in FIG. 3A, in one embodiment, the handheld controller 330 is attached to (inserted into) the handle 200 of the steerable probe 100. To that end, the handle 200 includes a tubular opening or receiving interface 202. In this configuration, minimal controls are accessible to the user. For example, only the first control section 331, such as a simple joystick or directional keypad is accessible to the user. This configuration is for manual insertion, so a simple joystick or directional keypad can provide the required functionality to control the tip of the probe (catheter or endoscope). Other controls, such as the buttons or switches for activating irrigation or suction (control section 332), are deactivated and/or hidden within the handle 200, thus eliminating the possibility of inadvertent activation and/or confusion by the user. An electrical connection between the handheld controller 330 and the handle 200 can be implemented via a contact connector 204 included within the handle 200. In the case where the buttons or switches of control section 332 are not hidden in the handle 332, the contact connector 204 may include a sensor (e.g., a pressure sensor or magnetic contact) which can detect the presence of the handheld controller 330 and thereby cause deactivation of the control section 332. In one or more embodiments where the contact connector 204 is a magnetic contact, a magnetic force can be used to secure attachment of the handheld controller 330 to the endoscope handle 200.

FIG. 3B shows another view of the configuration in which the handheld controller 330 is attached to (inserted into) the handle 200 of the probe 100, for manual control mode. In this configuration, a hand "H" of a user is gripping the handle 200. In this configuration, while the hand H of the user grabs the endoscope handle 200, since the handheld controller 330 is inserted into the receiving interface 202, the user can have access to the joystick control, for example, by using the thumb. However, other control buttons (control section 332) are not exposed to the hand of the user. Accordingly, the user can freely control the manual insertion of the probe 100 into a luminal cavity without worrying about accidentally touching the buttons of control section 332. Here, during manual operation, the probe movement in or out of the patient's cavity is user controlled, by manually pushing the handle 200 toward or pulling the handle 200 away from the patient, while observing an intra-operative image displayed on display device 420, as later explained in more detail.

FIG. 3C illustrates a configuration where the handle 200 of the probe 100 is attached to a robot support platform 350, and the handheld controller 330 is removed from the handle 200 for robot control mode (robotic mode). Once the endoscope handle 200 is docked on the support platform 350, the handheld controller 330 is removed and the control system 300 enters the robotic mode. Specifically, as shown in FIG. 3C, the handheld controller 330 is removable from the endoscope handle 200, and the endoscope handle 200 can be connected to the robotic control system 300 via a console video cable 220. To facilitate removal from the endoscope handle 200, the handheld controller 330 can be configured to "pop out" slightly from the handle 200 when the manual operation is completed, and/or when the handle 200 is placed on the support platform 350. For example, in the case where the handheld controller is magnetically attached to the handle 200, when the handle 200 is docked on the robot platform 350, the magnetic field can be interrupted and the handheld controller 330 can be configured to "pop out" slightly from the handle 200. In this manner, the user can be made aware that the handheld controller 330 is available for removal. In other embodiments, the handheld controller 330 can be configured to emit an aural or visual (e.g., a sound or light) or haptic (vibration) warning, so that the user is informed that the handheld controller 330 can be removed from the handle 200. In at least some embodiments, even after removed from the handle 200, the handheld controller 330 is configured to connect wirelessly (e.g., by a short range communication protocol such as Bluetooth protocol) with the handle 200.

In one or more embodiments, the handheld controller 330 enters a transition mode between the manual and robotic mode. A transition mode is a handoff mode in which the system senses the assembly status of the handheld controller 300 with respect to the handle 200. For example, when the manual operation is completed and/or when the handle 200 is placed on the support platform 350, the handheld controller's operation mode shifts from manual mode to the transition mode. In the transition mode all functions of the handheld controller are deactivated. While only accessible parts of the handheld controller 330 are activated in the manual mode, all of the joystick and control buttons are disabled in the transition mode. In the transition mode, the user can remove the handheld controller 330 from the handle 200. In this case where all functions are suppressed, the user can safely remove and hold the handheld controller 330 without accidentally pressing the control buttons or mistakenly actuating the joystick during the removal operation.

After having removed from the handle 200, and securely holding the handheld controller 330 with the user's hand, the system shifts the status of the controller from the transition mode to the robotic mode whereby the functions of the handheld controller 330 are restored.

<FIG. 4>

FIG. 4A, FIG. 4B, and FIG. 4C illustrate another embodiment of a hand controller 330. In this embodiment, the endoscope handle 200 is provided with hollow space (a cylindrical of tubular opening) forming a receiving interface 202 at the proximal end of the handle 200, to receive therein at least part of the handheld controller 330. The handheld controller 330 is made in the shape of a handle with an opening 335 configured to provide a gripping section 336 (grip handle) for the hand H of a user. To enter robotic mode, the user removes the handheld controller 330 by sliding it up in a lengthwise direction and out of the handle 200. When the handheld controller 330 is free of the handle 200, more controls on the controller 330 are accessible to the user.

More specifically, FIG. 4A shows a side view of the handheld controller 330 having a first control section 331 (e.g., a joystick or directional keypad) and a second control section 332 (e.g., control buttons or switches), which are similar to the control sections of handheld controller shown in FIG. 3A. The handheld controller 330 of FIG. 4A has a controller body with an elongated portion 333 which is configured to engage with the proximal opening (cylindrical opening) 202 (receiving interface) at the proximal end of the handle 200.

FIG. 4B shows the handheld controller 300 attached to the endoscope handle 200 at the proximal end thereof. In FIG. 4B, the handheld controller 330 is shown with the gripping portion 336 in the form of an opening 335 configured to allow the user's hand to firmly grip the handheld controller 330. FIG. 4C shows a benefit of providing the handheld controller 330 with the gripping portion 336, as the opening 335 of the gripping portion allows the user to pull the handheld controller 330 away from the endoscope handle 200 without touching other controls (i.e., without touching the buttons in a control section 332).

<FIG. 5>

FIG. 5A and FIG. 5B illustrate a further amendment of the handheld controller 330 configured to be removably attached to the handle 200. In this embodiment, the handheld controller 330 has an opening 337 configured to engage with a proximal receiving interface 203 (a cylindrical shaft) provided on the proximal end of the endoscope handle 200. In this manner, the handheld controller 330 is attached to the top of the endoscope handle 200 with the first control section 331 (joystick or keypad) readily accessible to the user, and second control section 332 (other controls) visible, but not accessible to the user. FIG. 5A shows the configuration for manual operation (manual mode), in which the user can access the first control section 331 (joystick or keypad) and the second control section 332 is deactivated. In this embodiment, an electrical connection between the handheld controller 300 and the handle 200 can be established by a connector 204 similar to that of FIG. 3A, but implemented in a different manner. For example, the cylindrical shaft of proximal receiving interface 203 may include electrical and/or magnetic contacts on the outer surface of the shaft, and the opening 337 can have corresponding electrical and/or magnetic contacts to create an electrical an/or magnetic connection when the controller is 330 is engaged with proximal end of the handle 200.

FIG. 5B shows the configuration for robotic operation (robotic mode) in which the handheld controller 330 is removed from the handle 200 and used as a handheld or finger held joystick. In the configuration of FIG. 5B, prior to the endoscope handle 200 being attached to the support platform (not shown), the user removes the controller 330 from the receiving interface 203 at top of the handle 200, and inserts a finger into the opening 337 for securely gripping the handheld controller 330. The user then uses the controller 330 like a wireless mini-ring joystick or a handheld directional keyboard. An example of a finger mini-joystick is commercially available as "ACGAM R1 Bluetooth 4.0 VR Wireless Gamepad Joystick Gaming Controller.

While this embodiment does not completely limit the user's physical accessibility to the second control section 332 like the other embodiments, the functions of the second control section 332 can be deactivated upon connection of the controller 330 with the handle 200. In one embodiment, deactivation of the control second control section 332 can be achieved by, for example, providing magnetic connector in the opening 337 which engages with the receiving interface 203. This configuration advantageously combines manual and robotic controls into one single controller device. In addition, although the second control section 332 is visible and could be (accidentally) touched by the user, the controller 330 can be configured such that the second control section 332 is deactivated when in manual mode. For example, in a different embodiment, a push button or switch (not shown) can be provided in the inside of the opening 337, so that when the controller 330 is mounted onto the receiving interface 203, such switch or push button deactivates the functions of the second control section 332.

<FIG. 6>

Figure 6:
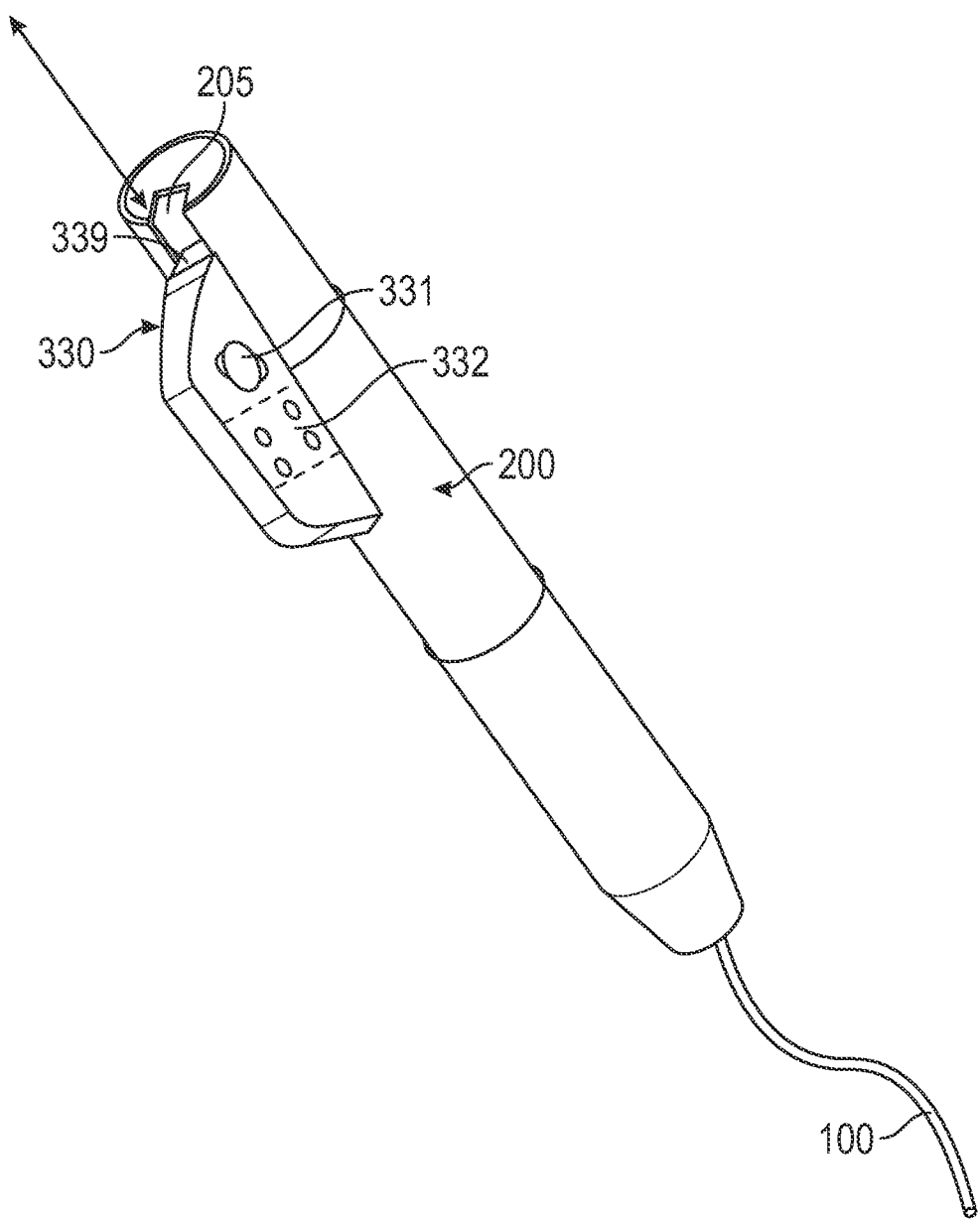
FIG. 6 shows a further embedment of a handheld controller 330 attachable to the endoscope handle 200 of a probe 100.

FIG. 6 illustrates another embodiment of the handheld controller 330 configured to be removably attached to the handle 200. As in the previous embodiments, the handheld controller 330 includes a first control section 331 and a second control section 332. According to the embodiment shown in FIG. 6, the handheld controller 330 can be docked and undocked from the endoscope handle 200 by sliding the controller 330 in and out of a channel or slot 205 formed on the outer surface of the endoscope handle 200. In other words, according to FIG. 6, the receiving interface for attaching the controller 330 to the handle 200 is provided by a slot 205 in the form of a linear groove or rail interface.

More specifically, in this embodiment, the handheld controller 330 is removably attached to the endoscope handle 200 by sliding down into channel or interface slot 205. This channel or slot 205 can be an open end slot made in the shape of a rail or groove on a side surface of the handle 200 in the lengthwise direction. And the handheld controller 330 can be provided with an engaging portion 339 in the form of an inverse T-shaped flange or other similar structure configured to engage with the slot 205. One or both of the slot 205 and engaging portion 339 can be made from a sturdy, low friction, plastic material, such as polyethylene, Teflon®, or polypropylene to provide a low coefficient of friction between the two members as they slide relative to one another to connect and disconnect the two components. Alternatively, as in previous embodiments, the handheld controller 330 can be magnetically connected to the handle 200. In this case too, an electrical connection between the handheld controller 330 and the handle 200 can be achieved by a connector 204 similar to that shown in FIG. 3A.

When the controller 330 is attached to the handle 200, the system is in manual mode. As in the previous embodiments, in the manual mode, only the control section 331 of the controller 330 is made available to the user for manually controlling the functions needed for manual insertion. In the manual mode, the second control section 332 is either hidden from the user or deactivated due to the connection between the handheld controller 330 and the handle 200. After the user manually inserts the probe 100 (catheter) into a patient, and removes the handheld controller 330, the system enters the robotic mode. The user removes the handheld controller by sliding it out of the interface slot 205. When the handheld controller 330 is disconnected from the endoscope handle 200, additional controls within the controller become accessible to the user. For example, during manual insertion, only the first control section 331 (e.g., a joystick or directional pad) is accessible to the user to control the steering of the tip of the probe 100. Then, after the handheld controller is removed from the endoscope handle 200, the second control section 332 (e.g., control buttons for irrigation or suction) becomes operational, in addition to the first control section 331. To that end, the handheld controller 330 can be provided with a switch (e.g., a non-illustrated spring or push switch) that deactivates the second control section 332 when the controller is inserted into the slot or channel 205.

The foregoing embodiments resolve the need for a seamless transition between manual insertion and robotic control of robotic endoscopic systems with an integrated controller. This novel solution overcomes the inconvenience of using two separate controllers (one for manual insertion and one for robotic navigation). This novel solution can prevent misplacement of one or both controllers, as well as prevent possible confusion about which controller to use at certain points of the workflow. Moreover, the combination handheld controller 330 and endoscope handle 200 disclosed herein provide a combined manual/robotic controller, without the possibility of confusion over which controls/functions are active at any given point during a procedure.

The design of the combined handheld controller 330 and endoscope handle 200 selectively limits accessibility of controlling features according to manual insertion or robotic navigation. Functionality is selectively accessible to the user only at the appropriate moment of the procedure workflow.

<FIG. 7>

Figure 7A:
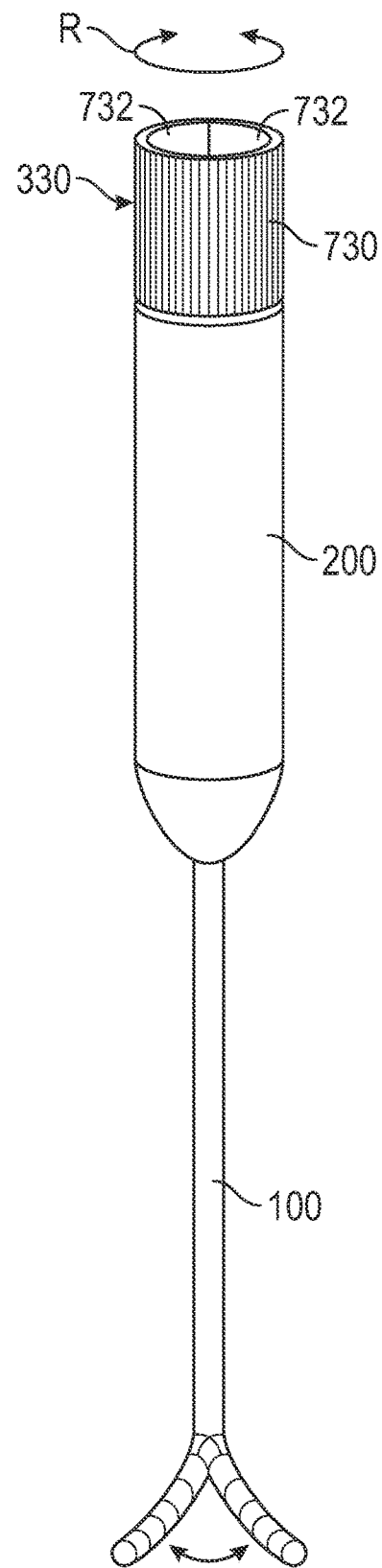
FIG. 7A, FIG. 7B, and FIG. 7C show a further embodiment of a handheld controller 330 combined with the endoscope handle 200.
Figure 7C:
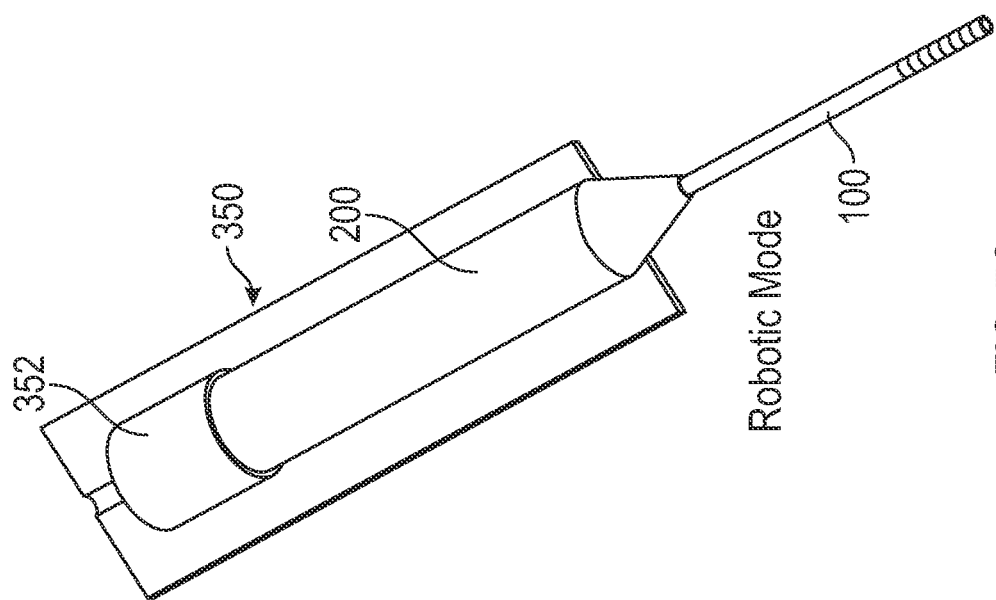
Figure 7B:
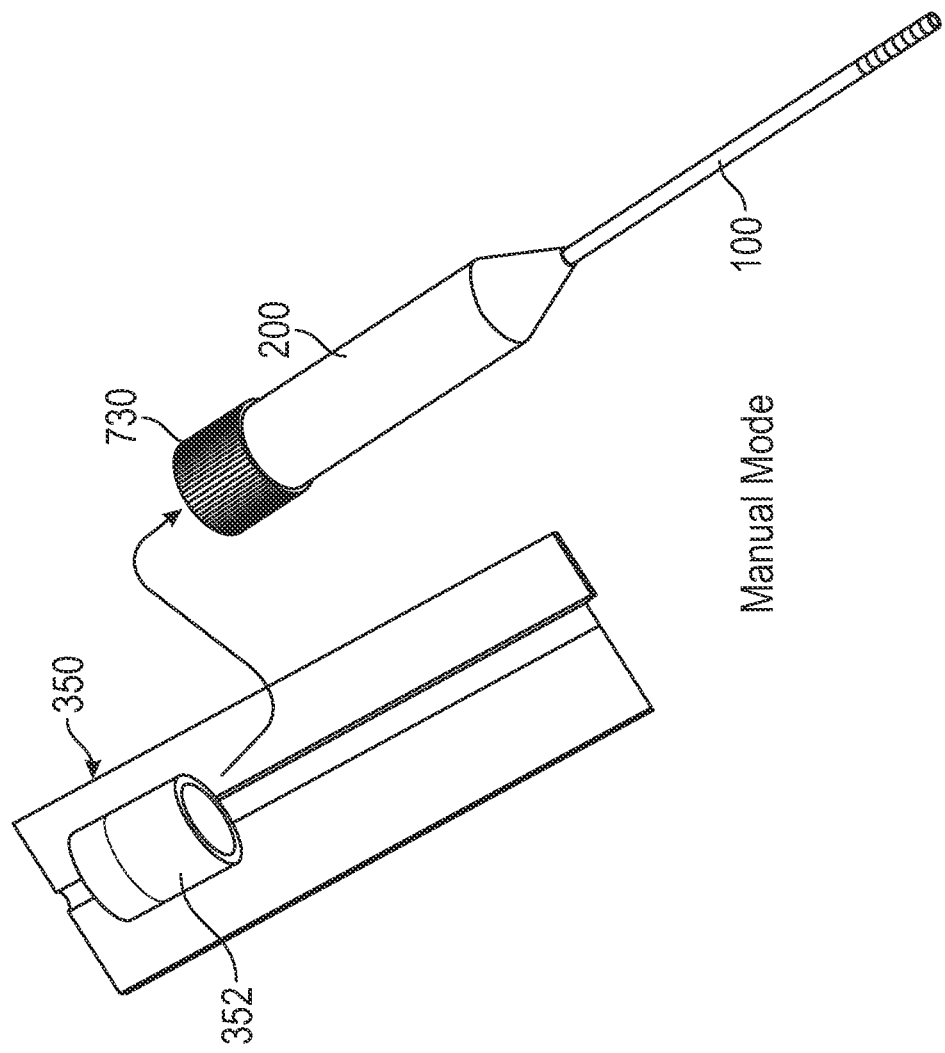

FIG. 7A, FIG. 7B, and FIG. 7C show a further embodiment of a handheld controller 330. According to the embodiment shown in FIG. 7A, the handheld controller 330 consists of a control knob 730 provided on top (proximal end) of the endoscope handle 200. In this embodiment, the control knob 730 is configured to turn (rotate) in either clockwise (CW) or counter-clockwise (CCW) directions by the user manually twisting the knob. This twisting of the knob 730 is programmed to correspond to the movement of the catheter tip, such that a twist of the knob to the left causes the tip to turn left, and a twist of the knob to the right causes the tip to turn right.

The control knob 730 provides a control signal when grasped by the fingertips of an operator and rotated either clockwise or counter-clockwise. To that end, the degree of rotation generally corresponds to the desired amount of control. Therefore, the control knob 730 of controller 330 may turn continuously or may have detents to produce discrete amounts of rotation. Typical electronic components of the control knob 730 may include potentiometers, variable capacitors, rotary switches, and combinations thereof. Desirably, the control knob 730 has a fixed "off" position where no control signal is provided. In addition, to provide additional functionality (e.g., for controlling irrigation, suction, or end effector operation), the controller 330 may include a plurality of push buttons or switches 732. As in previous embodiments, the controller 330 can be removable from the handle 200. In alternate embodiments, the controller 330 shown in FIG. 7A can be physically integrated with the handle 200 and non-removable.

FIG. 7B and FIG. 7C show the handheld controller 330 configured to be used with a robot support platform 350 without being removed from the handle 200. In this embodiment, the support platform 350 includes a controller receptacle 352. FIG. 7B shows the handheld controller 330 in manual operation mode. In manual mode, the handheld controller 330 is removed from the robot platform 350 and removed from the controller receptacle 352, so that the knob 730 is accessible to the user. In the robot mode, the combined handheld controller 330 and endoscope handle 200 are placed on the robot platform 350. As shown in FIG. 7C, in the robot mode, the control knob 730 is hidden inside the controller receptacle 352. Therefore, according to the present embodiment, the functions of the handheld controller 330 are not accessible to the user when the handle 200 is attached to the support platform 350.

During manual operation, probe movement in and out of the patient's anatomy is user controlled by manually pushing or pulling the handle 200 toward or away from the patient. This probe movement can be performed simultaneously with the manual operation of the control knob 730 to steer the tip of the probe 100.

The handheld controller 330 can be implemented in various configurations. For example, the control knob 730 might have knurls, a gripping texture, or other features to facilitate accurate rotation (twisting) of the controller. Preferably, the control knob 730 is symmetrical about the length axis, and substantially equal (slightly larger or smaller) in diameter to the handle 200.

The controller receptacle 352 is an opening for the manual control knob 730. It provides an interface between the support platform 350 and the endoscope handle 200. When the user inserts the control knob 730 into the receptacle 352, the system enters a robotically controlled mode (robotic mode), and the user does not have physical access to the control knob 730. This robotic mode configuration removes possible user confusion of using the manual controls to operate the probe when the system is in complete robotic mode.

Unlike the previous embodiments, the handheld controller 330 according to the present embodiment of FIG. 7A-7C does not require a control interface which protrudes from the surface of handle. Therefore, the integration of the control knob 730 into the general shape of the endoscope handle 200 is simplified, and facilitates easier mounting to the support platform 350.

Another advantage of the control knob 730 is that the rotational control can be mapped directly to the movement of the endoscope tip. That is, turning the knob left causes the endoscope tip to move left; and turning the knob right causes the tip to move right. This aspect improves the usability of the control mechanism because the manual control becomes more natural and intuitive for the user. This is a notable improvement of known controllers where the controlling feature typically provides for up/down controller movement or individual rotational dials to move the endoscope tip left/right. Additionally, the interface of the controller 330 with the support platform 350 (via the controller receptacle 352) ensures that the user cannot accidentally access the manual insertion controls while the system is in robotic mode. In this case, however, an additional controller can be necessary for completing an interventional procedure.

<FIG. 8>

FIG. 8A—FIG. 8C discloses an embodiment where the first control section 331 and the second control section 332 of the controller 330 are implemented as two separated controllers. The controller 330 shown and described above in reference to FIG. 7A-7C, will be considered as the first control section configured to control mainly the manual insertion of the endoscope probe 100 under manual mode. A second handheld controller 340 will be considered as the second control section configured to control the functions necessary to complete the interventional procedure under robotic mode.

FIG. 8A, FIG. 8B, and FIG. 8C show a method of using the steerable probe 100 in combination with the controller 330 and a handheld controller 340 in an robot system 300 configured to operate in either a manual mode or a robotic mode with a handoff transition mode between the two modes. In this embodiment, the system includes a robotic arm 800, a support platform 350, and an endoscope probe 100. The endoscope probe 100 is connected to an endoscope handle 200, and a controller 330 is attached to the handle 200. The handheld controller 340 is attached to the support platform 350 independent of the controller 330. As shown in FIG. 8A, in manual mode, the endoscope handle 200 is detached from the support platform 350; the controller 330 is attached to the handle 200; and the controller 340 remains attached to the support platform 350. In manual mode, the user manually inserts the endoscopic probe 100 and steers the tip of the probe using the exposed knob 730 (of controller 330) provided at the proximal end of the endoscope handle 200. During manual insertion, the probe 100 transmits endoscopic images to the computer system 400 via a video cable 220. Therefore, the user can observe the images and the manual operation using a display device 420 (monitor) mounted on the cart, boom, wall, or on the platform 350 of the system. After the manual insertion, the user returns the endoscope handle 200 along with the controller 330 to the support platform 350, as shown in FIG. 8B.

FIG. 8B shows a transition or handoff mode in which the endoscope handle 200 together with the controller 330 are attached back onto the support platform 350. In the transition mode, as soon as the manual insertion of the probe is completed and/or when the user places the handle 200 back on the support platform 350, the system transitions to a handoff mode. For example, in this handoff or transition mode, the controller 330 becomes inaccessible and the second controller 340 becomes active.

FIG. 8C shows the robotic mode in which the handle 200 now remains attached to the support platform 350 and the controller 330 is hidden from the user or deactivated. When the controller 330 is implemented by a control knob 730 as shown in FIG. 7A, the controller 330 is hidden in the controller receptacle 352, and thus is not accessible to the user. The probe 100 transmits endoscopic images to the system via the video cable 220. In the robotic mode, once the handle 200 is placed on the support platform, the handheld controller 340 now becomes active and is ready for use during robotic navigation. The handheld controller 340 can be wired or wireless and can be detachable from the platform 350. In other words, there is a seamless transition from using the handheld controller 330 and handle 200 for manual probe insertion to using the robot support platform 350 and the second handheld controller 340 for robotic navigation of the endoscope probe 100.

<FIG. 9>

Figure 9:
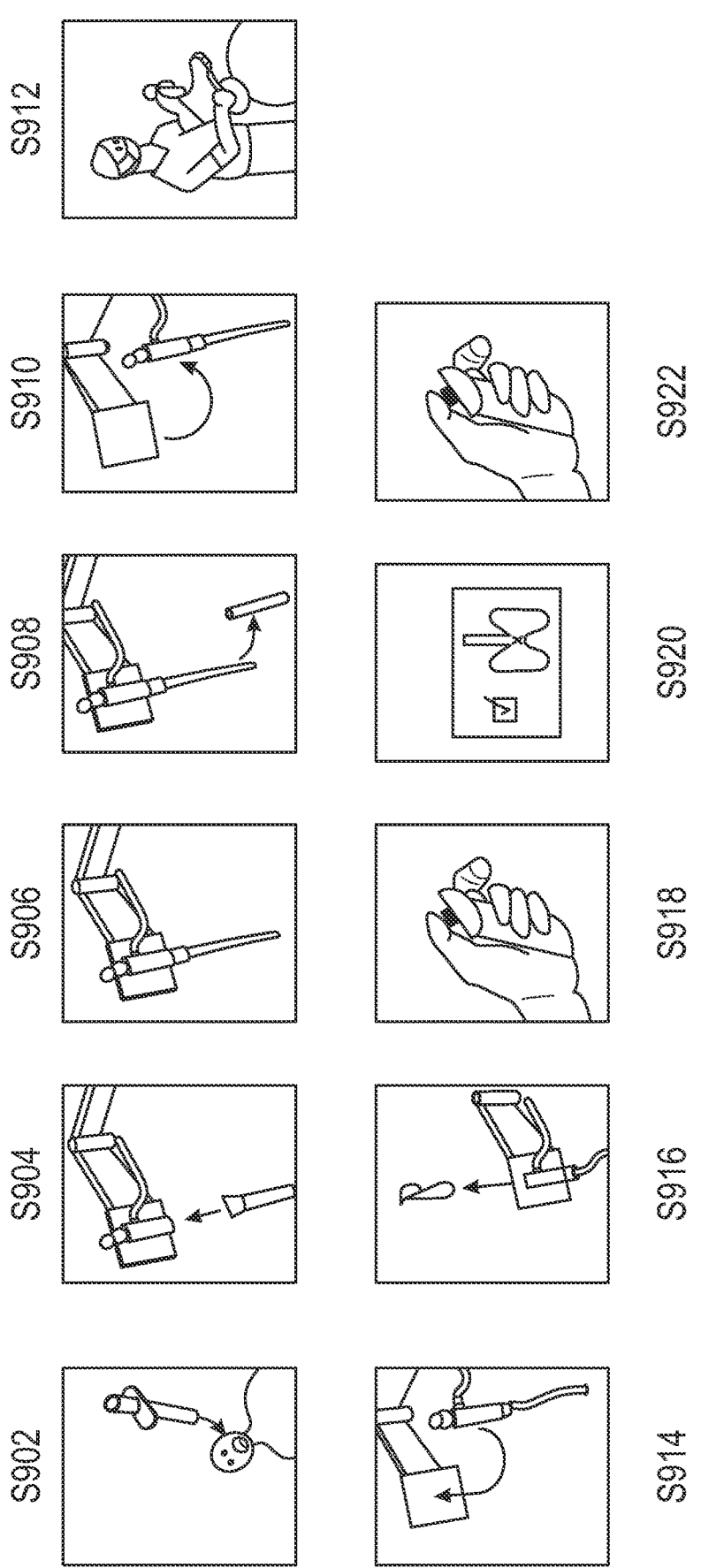
FIG. 9 shows an exemplary workflow which defines a process (method) for manual insertion and robotically controlled navigation using the handheld controller 330 in combination with the endoscope handle 200.

FIG. 9 shows an exemplary workflow which defines a process (method) for manual insertion and robotically controlled navigation using the handheld controller according to one or more of the various embodiments described above. According to the workflow of FIG. 9, at step S902, a patient preparation step occurs. For example, the user (an endoscopist) manually inserts an endotracheal tube into a patient. At step S904, the user attaches a new (sterile) catheter or probe 100 to the handle 200 which is already attached to the support platform 350. The new catheter or probe 100 is generally provided in a straight packaging sleeve. In addition, at step S904, the handheld controller 330 is attached to the handle 200. Next, at step S906, an auto-calibration process occurs. At step S906, because the catheter or probe 100 is in a straight packaging sleeve, the system can calibrate the positions of the control wires within the probe to a mean straight catheter position—essentially an operation analogous to a "tare" on a scale, so that probe navigation can start from a known reference (initial position and/or orientation).

At step S908, the user removes the straight packaging sleeve from the sterile catheter or probe 100. At step S910, the user removes the handle 200 and controller 330 from the support platform 350, and carries the assembled probe 100 to the patient. At step S912, the user manually inserts the catheter to a predetermined location using manual steering controls available through the controller 330. For example, for a bronchoscopy, the user manually inserts the catheter or probe 100 to the first carina while steering the tip of the probe with the joystick or control knob of the handheld controller 330. In this step, the user may use the image displayed by system to confirm if the tip of the probe is at the desired predetermined location. For example, an image similar to that of S920 is provided to the user on the display device 420 throughout the manual and robotic operations. After reaching the predetermined location, at step S914, the user attaches the handle 200 back onto the support arm 350. At step S916, the user can detach the handheld controller 330 from the handle 200 to enter the robotic mode. Alternatively, at step S916, the system automatically transitions to robotic mode, and informs the user of the availability of the handheld controller 330, as previously described above. At step S918, under robotic mode, the user can use the joystick or knob controller of the handheld controller 330 to navigate the tip of the probe 100 to the desired destination using on-screen endoscopic images and necessary software navigation. To that end, at step S920, the user may wish to first confirm the location of the tip of the probe 100 with respect to the desired target. For example, the user confirms if the tip of the probe is at the desired predetermined location (e.g., first carina). Then at step S922, the user navigates the probe 100 to the target location using the handheld controller 330 in robot mode.

Next, an example of robotic navigation of the steerable probe 100 is explained. In general, either during insertion or retraction of the steerable probe 100 through a patient's anatomy, the center line of the lumen (e.g., the center line of an airway) is the desired trajectory to be followed during active control of the bending segments of the steerable section 101 (refer to FIG. 1A-1B). To that end, known guiding techniques of steerable instruments, such as robotic guided catheters or endoscopes, can be used. In general, various known concepts of shaft guidance robotically operate the steerable instrument with the goal of forcing the flexible shaft to keep to a desired trajectory. In one such example, when using robotic navigation, the steerable instrument is advanced through a lumen while sensors measure the insertion depth of the shaft-guide and the angulations of user-controlled steerable tip segments to obtain trajectory information. The trajectory information is stored in a memory of the system and continuously updated. After a short advance in insertion depth, the shape of the steerable shaft-guide is corrected by adjusting (rotating, twisting, or bending) segments of the instrument in such a way that the new shape closely matches the desired trajectory. This process is repeated until a target area is reached. The same process is applied when the steerable instrument is withdrawn from the patient's lumen. See, e.g., US 2007/0135803, which is incorporated by reference herein for all purposes.

<FIG. 10>

Figure 10:
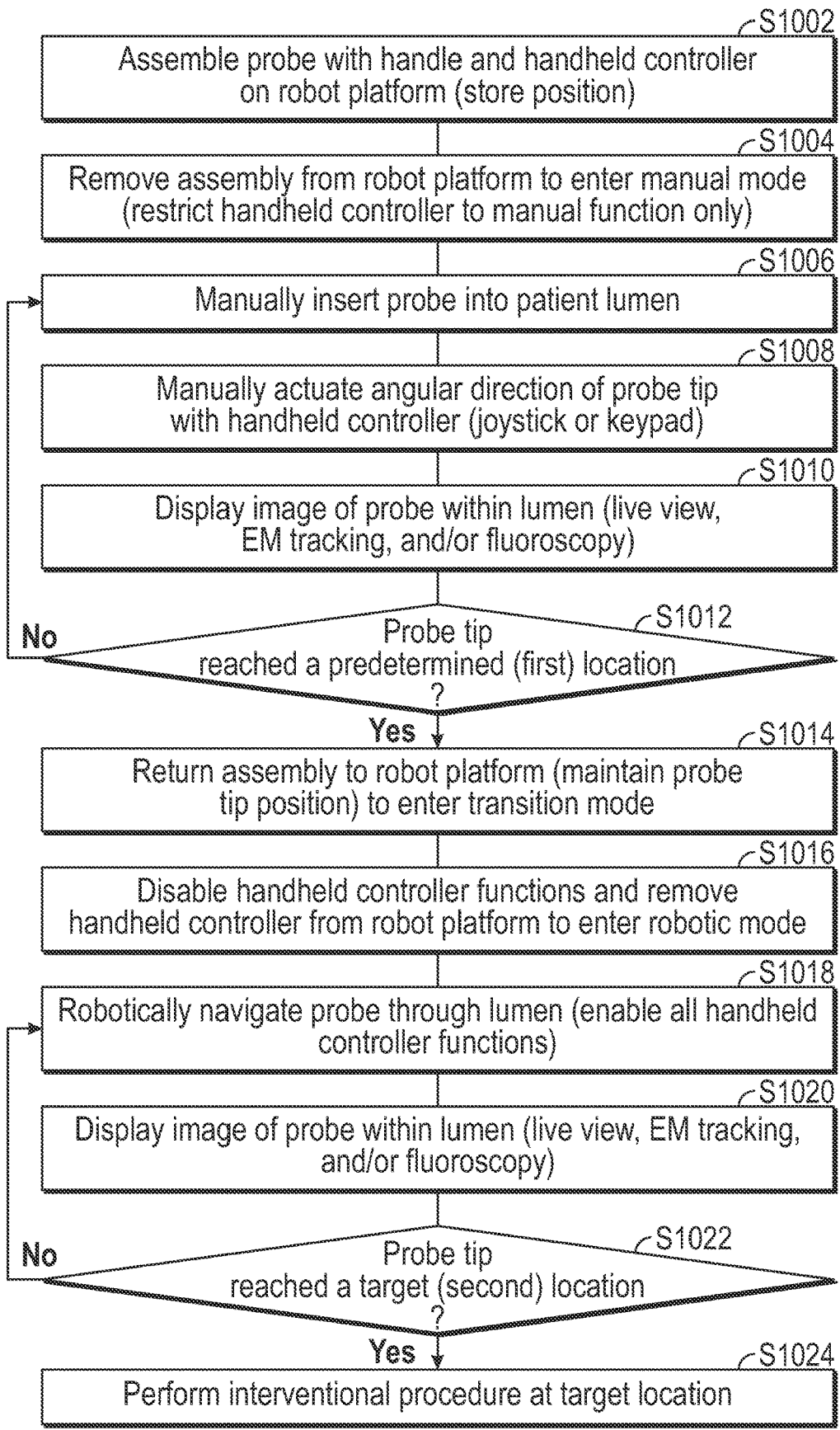
FIG. 10 shows a workflow process for controlling a steerable probe 100 to selectively operate either in manual mode or robotic mode with a handheld controller either coupled to or decoupled from the endoscope handle 200.

FIG. 10 illustrates a workflow process (an algorithm) for controlling a steerable probe 100 to selectively operate either in manual mode or in robotic mode. First, at step S1002, the workflow requires an assembly process to assemble the steerable probe 100 with the handle 200 and the handheld controller 330 on the support platform 350 (robot platform). As explained with reference to S904-908 of FIG. 9, as this step, the handheld controller 330 is attached to the handle 200, and an auto-calibration process is carried out, so that probe navigation can start from a known reference (initial position and/or orientation). This initial position and/or orientation of the probe assembly with respect to patient is stored in the system's memory, and remains continuously monitored and updated throughout the procedure (e.g., by EM tracking).

At step S1004, the combined assembly of the handheld controller (330) with the handle 200 attached to the probe 100 is removed from the support platform 350. Here, when the handheld controller 330 is combined with the handle 200, certain functions of the handheld controller are restricted, and only functions required for manual operation are active in the controller 330. All functions other than those used for manual operations are restricted by being hidden within the handle 200 or deactivated by the system controller. Therefore, when the assembly is removed from the robot platform, the system enters a manual control mode (manual mode).

In the manual mode, at step S1006, the operator can safely insert the probe 100 into a patient lumen. At step S1008, as the probe is manually advanced through the patient lumen, the user actuates the probe tip direction using the manual controls (first control section 331) without worrying about accidentally operating functions other than manual steering of the probe tip. At step S1010, during manual insertion and actuation of the probe tip, the system continuously displays a probe advancement image. The image displayed during probe insertion can be a live-view image acquired in real-time by an imaging device (e.g., an endoscope camera) arranged in the probe. Alternatively or in addition, the image displayed during probe insertion can be an intra-operative image provided by electromagnetic field (EM) tracking and/or fluoroscopy imaging combined with a pre-operative image (e.g., MRI or CT) image of the patient anatomy. At step S1012, based on the displayed image and/or other positional information (e.g., EM tracking information), the software system or the user can make a determination as to whether the tip of the probe has reached a predetermined location (first location) within the lumen. In a bronchoscopy procedure, the first location can be the first carina in the airway of a patient (subject). The process of steps S1006-S1012 is repeated until the probe tip is manually navigated to the desired predetermined or first location.

At step S1012, when the user confirms that probe has reached the predetermined or first location (YES in S1012), the user stops the manual insertion. Here, the system can be configured to provide a confirmation to the user, for example, by displaying a confirmation image as shown in S920 of FIG. 9. At step S1014, similar to S914 of FIG. 9, the user returns (reattaches) the assembly of probe 100 together with the handle 200 and handheld controller 330 to the robotic support platform 350. When the user returns the assembly to the support platform 350, care must be taken to make sure that the probe tip remains at the first location. Therefore, the system enters a transition mode. In the transition mode, to avoid unintended or accidental manual actuation of the probe via the handheld controller, it may be advantageous to disable all functions of the handheld controller 330.

Between the manual and robotic modes, user needs to reattach the handle to the support platform, and then detach handheld controller from handle and hold only handheld controller. Either when reattaching the handle to the platform, or when detaching the handheld controller from the handle, there may be a situation the user might mistakenly hit a finger to the joystick and bend the catheter mistakenly. Therefore, it is advantageous to have a transition mode in which all of the handheld controller's input functions are disabled. In this manner, the user can safely detach the handheld controller from the handle.

At step S1016, after the functions of the handheld controller 330 are disabled, the user removes the handheld controller 330 from the support platform 350. After the user removes the handheld controller 330 from the support platform 350, the system enters the robotic control mode (robotic mode). As described above, the robotic mode includes the process of probe navigation based on programmed software applications (e.g., based on kinematic models). At this stage of the workflow, navigation is controlled by the robotic controller 302 and associated software. However, at least certain robotic functions (second control section 332) of the handheld controller also become available to the user. Therefore, at step S1018, the user follows the robotic navigation and uses all of the functions available through the handheld controller 330 and/or through the robotic controller 302 to advance the tip of probe 100 through the patient lumen. At step S1020, the system again displays a probe advancement image, which can be a live-view image and/or a pre-operative image combined with positional information, or combinations thereof. At step S1022, the user or the system itself makes a determination as to whether the tip of probe 100 has reached its final or target location (second location). The target or second location can be, for example, a tumor or an anatomy of the patient where an interventional procedure should be carried out by one or more tools guided through the probe. More specifically, the target location can be a target in or around the lumen where one or more end effectors attached to (or inserted trough) the probe can be operated to carry out an interventional procedure. The process of steps S1018 to S1022 can be repeated until the probe tip is confirmed to have reached the target location. At step S1024, after the system confirms that the probe 100 is correctly positioned at the target location, the user can be prompted to complete the necessary interventional procedure.

After the interventional procedure is completed, it is a matter of course that the robotic mode is also applied to the withdrawal of the probe 100 from the patient's anatomy through the lumen. In this regard, it is also possible that the system can transition from the robotic mode to a manual mode during withdrawal (extraction) of the probe from the patient anatomy. For example, after the procedure is completed, the robotic mode can be used to safely withdraw the probe from the second location to the first location of the lumen, and thereafter the system can transition to the manual mode where the probe can be removed manually by using only the manual functions of the handheld controller 330.

The foregoing disclosure describes a handheld controller for combined manual insertion and robotic mode control. This device has a handle to grip while manually inserting the catheter to a predetermined location (e.g., the first carina of the lungs.) After manual insertions, the handle is attached to a support platform. This initiates robotic mode, where the insertion/retraction is controlled and moved by the support platform of the robotic system. When the system is in robotic mode, the handheld controller is detached from the handle and is used to control the system. The attachment of the handheld controller to the handle is such that only controls appropriate to a particular portion of the system workflow are exposed to the user at a given time. This novel handheld controller and modes of use lessens possible confusion over which controls/functions are active at any given point during a procedure. This is a potential cost savings over two separate controllers. More over the novel features this controller, in most of the embodiments, also selectively governs the accessibility of controlling features. Functionality is accessible by the user only at the appropriate moment the procedure workflow.

Software Related Disclosure

Embodiment(s) of the present disclosure can be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like. An I/O interface can be used to provide communication interfaces to input and output devices, which may include a keyboard, a display, a mouse, a touch screen, touchless interface (e.g., a gesture recognition device) a printing device, a light pen, an optical storage device, a scanner, a microphone, a camera, a drive, communication cable and a network (either wired or wireless).

Other Embodiments, Modifications, Combinations and/or Alterations

In referring to the description, specific details are set forth in order to provide a thorough understanding of the examples disclosed. In other instances, well-known methods, procedures, components and circuits have not been described in detail as not to unnecessarily lengthen the present disclosure. Unless defined otherwise herein, all technical and scientific terms used herein have the same meaning as commonly understood by one of ordinary skill in the art to which this invention belongs. The scope of the present disclosure is not to be limited by the subject specification and drawing, but rather only by the plain meaning of the claim terms employed.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

While the present disclosure has been described with reference to exemplary embodiments, it is to be understood that the present disclosure is not limited to the disclosed exemplary embodiments. The scope of the following claims is to be accorded the broadest interpretation so as to encompass all such modifications and equivalent structures and functions.

What is claimed is:

1. A system configured to control an endoscope probe to selectively operate either in a manual mode or in a robotic mode, the controller system comprising:
    a handle arranged at a proximal portion of the probe and configured to transmit an actuating force from an actuator to a distal portion of the probe;
    a handheld controller attachable to the handle; and
    a robotic controller in communication with the handle and/or with the handheld controller,
    wherein, in the manual mode, the handheld controller is combined with the handle, and the combined handheld controller and handle are configured to be operated by a user to manually insert and actuate the distal portion of the probe into a lumen of a subject,
    wherein, in the robotic mode, the robotic controller is connected with the handle and configured to robotically control navigation and actuation of the probe within the lumen,
    wherein the handheld controller includes a first control section configured to operate in the manual mode, and a second control section configured to operate in the robotic mode,
    wherein the first control section of handheld controller includes a joystick configured to control angular movement of the probe, and the second control section includes controls for irrigation and/or suction performed during an interventional procedure through the probe, and
    wherein, in the manual mode, the joystick is configured to control only manual angulation movement of the distal portion of the probe, while the controls for irrigation and/or suction are disabled and/or hidden within the handle.

2. The system according to claim 1,
    wherein, in the robotic mode, the handheld controller is detached from the handle, and
    wherein handheld controller remains in communication with to the robotic controller via a wired or wireless connection.

3. The system according to claim 1,
    wherein the robotic controller is further configured to control the endoscope probe in a transition mode in which the manual mode transitions into the robotic mode or vice versa,
    wherein, in the transition mode, both the first control section and the second control section of the handheld controller are not operable by the user.

4. A system configured to control an endoscope probe to selectively operate either in a manual mode or in a robotic mode, the system comprising:
    a handle arranged at a proximal portion of the probe and configured to transmit an actuating force from an actuator to a distal portion of the probe;
    a handheld controller attachable to the handle; and
    a robotic controller in communication with the handle and/or with the handheld controller,
    wherein, in the manual mode, the handheld controller is combined with the handle, and the combined handheld controller and handle are configured to be operated by a user,
    wherein, in the robotic mode, the robotic controller is connected with the handle and configured to robotically control navigation and actuation of the probe within the lumen,
    wherein a first control section of the handheld controller includes a directional keypad having controls for angular movement of the probe, and a second control section includes push buttons or switches for irrigation and/or suction performed during an interventional procedure though the probe, and
    wherein, in the manual mode, the directional keypad is configured to control only manual angular movement of the distal portion of the probe, while the push buttons or switches for irrigation and/or suction are disabled and/or hidden within the handle.

5. The system according to claim 4,
    wherein the handheld controller includes a connecting portion configured to connect with the handle and a gripping portion configured to be held by a hand of the user.

6. The system according to claim 5,
    wherein the handheld controller is configured to be attached to and detached from the handle, and
    wherein the handheld controller is attachable to the handle by sliding the connecting portion of the handheld controller into a receiving interface formed on a portion of the handle, and the handheld controller is detachable from the handle by sliding the connecting portion out of the receiving interface.

7. The system according to claim 5,
    wherein the receiving interface is a linear slot formed in a lengthwise direction on an outer surface of the handle, and
    wherein the connecting portion of the handheld controller is configured to engage with and disengage from the linear slot formed on the outer surface of the handle.

8. The system according to claim 7,
    wherein the linear slot formed on the outer surface of the handle is an open end linear slot, and
    wherein the connecting portion of the handheld controller is configured to engage and disengage by sliding through the open end of the linear slot formed on the outer surface of the handle.

9. The system according to claim 7,
    wherein, when the handheld controller is attached to the linear slot formed on the outer surface of the handle, the handheld controller operates in the manual mode, and wherein, in the manual mode, the second control section of handheld controller is deactivated and only the first control section of the handheld controller is accessible to the user for controlling the manual insertion and actuation of the probe into the lumen, wherein, when the handheld controller is detached from the linear slot formed on the outer surface of the handle, the handheld controller operates in the robotic mode, and wherein, in the robotic mode, the second control section of the handheld controller is accessible to the user for controlling functions of an interventional procedure performed through the probe within the lumen.

10. The system according to claim 5, wherein the receiving interface is a tubular opening formed at the proximal end of the handle, and wherein the connecting portion of the handheld controller is a tubular shaft configured to be docked on and undocked from the tubular opening formed at the proximal end of the handle.

11. The system according to claim 10, wherein, when the handheld controller is docked on the tubular opening formed at the proximal end of the handle, the handheld controller operates in the manual mode, and only the first control section of the handheld controller is accessible to the user for controlling movement and actuation functions needed for manual insertion of the probe into the lumen, and wherein, when the handheld controller is undocked from the tubular opening formed at the proximal end of the handle, the handheld controller operates in the robotic mode, and only the second control section of the handheld controller is available to the user for controlling functions of an interventional procedure performed through the probe within the lumen.

12. The system according to claim 5, wherein the receiving interface is a cylindrical shaft formed at the proximal end of the handle, and wherein the connecting portion of the handheld controller includes a cylindrical opening configured to be docked on and undocked from the cylindrical shaft formed at the proximal end of the handle.

13. The system according to claim 12, wherein, when the handheld controller is docked on the cylindrical shaft formed at the proximal end of the handle, the handheld controller operates in the manual mode, and only the first control section of the handheld controller is accessible to the user for controlling displacement and actuation of the probe during manual insertion of the probe into the lumen, and wherein, when the handheld controller is undocked from the cylindrical shaft formed at the proximal end of the handle, the handheld controller operates in the robotic mode, and only the second control section of the handheld controller is accessible to the user for controlling functions of an interventional procedure performed through the probe within the lumen.

14. The system according to claim 1, further comprising:

a robotic platform configured to support therein one or more of the handheld controller, the handle and the probe combined with each other in a positional relation for an interventional procedure in the lumen of a subject, wherein the robotic controller stores, in a memory of the system, the positional relation of the handheld controller, the handle and the probe combined with each other.

\* \* \* \* \*